United States Patent
Bell et al.

(10) Patent No.: US 11,786,371 B2
(45) Date of Patent: Oct. 17, 2023

(54) MODULAR VALVE PROSTHESIS, DELIVERY SYSTEM, AND METHOD OF DELIVERING AND DEPLOYING A MODULAR VALVE PROSTHESIS

(71) Applicant: Medtronic Vascular, Inc., Santa Rosa, CA (US)

(72) Inventors: Rodney Bell, Ballybrit (IE); Declan Costello, Ballybrit (IE); Niall Duffy, Ballybrit (IE); Frank Harewood, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 636 days.

(21) Appl. No.: 16/783,944

(22) Filed: Feb. 6, 2020

(65) Prior Publication Data
US 2020/0170796 A1     Jun. 4, 2020

Related U.S. Application Data

(62) Division of application No. 15/186,593, filed on Jun. 20, 2016, now Pat. No. 10,588,745.

(51) Int. Cl.
*A61F 2/24* (2006.01)
*A61F 2/852* (2013.01)

(52) U.S. Cl.
CPC .......... *A61F 2/2436* (2013.01); *A61F 2/2412* (2013.01); *A61F 2/2418* (2013.01);
(Continued)

(58) Field of Classification Search
CPC .... A61F 2/2436; A61F 2/2412; A61F 2/2418; A61F 2/852; A61F 2/2439; A61F 2/89; A61F 2250/0018; A61F 2250/006
See application file for complete search history.

(56) References Cited

U.S. PATENT DOCUMENTS

| 3,574,865 A | 4/1971 | Hamaker |
| 3,997,923 A | 12/1976 | Possis |

(Continued)

FOREIGN PATENT DOCUMENTS

| EP | 3072478 | 9/2016 |
| WO | WO2007081820 | 7/2007 |

(Continued)

OTHER PUBLICATIONS

International Search Report in PCT/US2017/035785, dated Dec. 1, 2017.

*Primary Examiner* — Sarah A Long
(74) *Attorney, Agent, or Firm* — Medler Ferro Woodhouse & Mills PLLC

(57) ABSTRACT

A modular valve prosthesis includes an inflow stent, a valve component including a valve stent and a prosthetic valve, and an outflow stent. In a radially compressed delivery configuration, an inflow end of the valve stent is separated from an outflow end of the inflow stent and an outflow end of the valve stent is separated from an inflow end of the outflow stent. In a radially expanded deployed configuration, the inflow end of the valve stent is in contact with the outflow end of the inflow stent and the outflow end of the valve stent is in contact with the inflow end of the outflow stent. A delivery system includes a capsule including first, second and third sections and flexible first and second bands between respective sections. The modules of the modular valve prosthesis are aligned with the sections and gaps between the modules are aligned with the bands.

13 Claims, 21 Drawing Sheets

(52) U.S. Cl.
CPC ........ *A61F 2/852* (2013.01); *A61F 2250/006* (2013.01); *A61F 2250/0018* (2013.01)

(56) References Cited

U.S. PATENT DOCUMENTS

| | | | |
|---|---|---|---|
| RE31,040 E | 9/1982 | Possis | |
| 4,506,394 A | 3/1985 | Bedard | |
| 4,705,516 A | 11/1987 | Barone et al. | |
| 4,790,843 A | 12/1988 | Carpentier et al. | |
| 5,032,128 A | 7/1991 | Alonso | |
| 5,332,402 A | 7/1994 | Teirelbaum | |
| 5,370,685 A | 12/1994 | Stevens | |
| 5,716,370 A | 2/1998 | Williamson, IV et al. | |
| 5,984,959 A | 11/1999 | Robertson et al. | |
| 6,074,408 A | 6/2000 | Freeman | |
| 6,106,550 A | 8/2000 | Magovern et al. | |
| 6,176,877 B1 | 1/2001 | Buchanan et al. | |
| 6,217,611 B1 | 4/2001 | Klostermeyer | |
| 6,419,696 B1 | 7/2002 | Ortiz et al. | |
| 6,425,916 B1* | 7/2002 | Garrison ............... | A61F 2/2436 623/2.11 |
| 6,468,305 B1 | 10/2002 | Otte | |
| 6,530,952 B2 | 3/2003 | Vesely | |
| 6,569,196 B1 | 5/2003 | Vesely | |
| 6,730,121 B2 | 5/2004 | Ortiz et al. | |
| 6,764,508 B1 | 7/2004 | Roehe et al. | |
| 6,786,925 B1 | 9/2004 | Schoon et al. | |
| 6,790,229 B1 | 9/2004 | Berreklouw | |
| 6,846,325 B2 | 1/2005 | Liddicoat | |
| 6,896,459 B1 | 5/2005 | Bullock | |
| 6,908,481 B2 | 6/2005 | Cribier | |
| 6,939,365 B1 | 9/2005 | Fogarty et al. | |
| 6,964,684 B2 | 11/2005 | Ortiz et al. | |
| 7,011,681 B2 | 3/2006 | Vesely | |
| 7,097,659 B2 | 8/2006 | Woolfson et al. | |
| 7,147,663 B1 | 12/2006 | Berg et al. | |
| 7,172,625 B2 | 2/2007 | Shu et al. | |
| 7,186,265 B2 | 3/2007 | Sharkawy et al. | |
| 7,252,682 B2 | 8/2007 | Seguin | |
| 7,291,168 B2 | 11/2007 | Macoviak et al. | |
| 7,300,463 B2 | 11/2007 | Liddicoat | |
| 7,311,730 B2 | 12/2007 | Shlomo | |
| 7,381,220 B2 | 6/2008 | Macoviak et al. | |
| 7,503,930 B2 | 3/2009 | Sharkawy et al. | |
| 7,513,909 B2 | 4/2009 | Lane et al. | |
| 7,527,646 B2 | 5/2009 | Rahdert et al. | |
| 7,578,843 B2 | 8/2009 | Shu | |
| 7,585,321 B2 | 9/2009 | Bribier | |
| 7,597,711 B2 | 10/2009 | Drews et al. | |
| 7,611,535 B2 | 11/2009 | Woolfson et al. | |
| 7,648,528 B2 | 1/2010 | Mikolaj | |
| 7,691,144 B2 | 4/2010 | Chang et al. | |
| 7,708,775 B2 | 5/2010 | Rowe et al. | |
| 7,717,955 B2 | 5/2010 | Lane et al. | |
| 7,722,667 B1 | 5/2010 | Buchanan | |
| 7,758,640 B2 | 7/2010 | Vesely | |
| 7,771,469 B2 | 8/2010 | Liddicoat | |
| 7,776,083 B2 | 8/2010 | Vesely | |
| 7,846,203 B2 | 12/2010 | Cribier | |
| 7,846,204 B2 | 12/2010 | Letac | |
| 7,887,583 B2 | 2/2011 | Macoviak | |
| 7,951,197 B2 | 5/2011 | Lane et al. | |
| 7,959,674 B2 | 6/2011 | Shu et al. | |
| 7,981,153 B2 | 7/2011 | Fogarty et al. | |
| 8,002,825 B2 | 8/2011 | Letac | |
| 8,025,695 B2 | 9/2011 | Fogarty et al. | |
| 8,052,750 B2 | 11/2011 | Tuval | |
| 8,057,540 B2 | 11/2011 | Letac | |
| 8,070,800 B2 | 12/2011 | Lock | |
| 8,083,793 B2 | 12/2011 | Lane et al. | |
| 8,105,377 B2 | 1/2012 | Liddicoat | |
| 8,142,496 B2 | 3/2012 | Berreklouw | |
| 8,163,013 B2 | 4/2012 | Machold et al. | |
| 8,187,207 B2 | 5/2012 | Machold et al. | |
| 8,236,049 B2 | 8/2012 | Rowe et al. | |
| 8,308,798 B2 | 11/2012 | Pintor et al. | |
| 8,323,335 B2 | 12/2012 | Rowe et al. | |
| 8,398,708 B2 | 3/2013 | Meiri et al. | |
| 8,486,132 B2* | 7/2013 | Snow ...................... | A61F 2/915 623/1.11 |
| 8,500,798 B2 | 8/2013 | Rowe et al. | |
| 8,551,160 B2 | 10/2013 | Figulla et al. | |
| 8,551,161 B2 | 10/2013 | Dolan | |
| 8,591,573 B2 | 11/2013 | Barone | |
| 8,591,575 B2 | 11/2013 | Bribier | |
| 8,597,348 B2 | 12/2013 | Rowe et al. | |
| 8,657,872 B2 | 2/2014 | Seguin | |
| 8,685,086 B2 | 4/2014 | Navia et al. | |
| 8,747,460 B2 | 6/2014 | Tuval et al. | |
| 8,771,345 B2 | 7/2014 | Tuval | |
| 8,771,346 B2 | 7/2014 | Tuval et al. | |
| 8,834,561 B2 | 9/2014 | Figulla | |
| 8,840,663 B2* | 9/2014 | Salahieh ............... | A61F 2/2418 623/2.17 |
| 8,840,664 B2 | 9/2014 | Karapetian et al. | |
| 2001/0010017 A1 | 7/2001 | Letac | |
| 2004/0093061 A1 | 5/2004 | Acosta et al. | |
| 2005/0137686 A1 | 6/2005 | Salahieh et al. | |
| 2005/0137691 A1 | 6/2005 | Salahieh et al. | |
| 2005/0203616 A1 | 9/2005 | Cribier | |
| 2006/0195183 A1 | 8/2006 | Navia et al. | |
| 2006/0287717 A1 | 12/2006 | Rowe et al. | |
| 2007/0010876 A1 | 1/2007 | Salahieh et al. | |
| 2007/0016288 A1* | 1/2007 | Gurskis ................. | A61F 2/2418 623/2.11 |
| 2007/0219613 A1* | 9/2007 | Kao ................. | A61B 17/12022 623/1.11 |
| 2009/0125098 A1 | 5/2009 | Chuter | |
| 2009/0281609 A1 | 11/2009 | Benichou et al. | |
| 2010/0036479 A1 | 2/2010 | Hill et al. | |
| 2010/0179648 A1 | 7/2010 | Richter et al. | |
| 2010/0179649 A1 | 7/2010 | Richter et al. | |
| 2010/0185275 A1 | 7/2010 | Richter et al. | |
| 2010/0249894 A1 | 9/2010 | Oba et al. | |
| 2010/0280606 A1 | 11/2010 | Naor | |
| 2010/0312333 A1 | 12/2010 | Navia et al. | |
| 2011/0224785 A1 | 9/2011 | Hacohen | |
| 2011/0251680 A1 | 10/2011 | Tran et al. | |
| 2012/0022640 A1 | 1/2012 | Gross et al. | |
| 2012/0046741 A1 | 2/2012 | Tuval et al. | |
| 2012/0059458 A1 | 3/2012 | Buchbinder | |
| 2012/0083839 A1 | 4/2012 | Letac | |
| 2012/0101571 A1 | 4/2012 | Thambar et al. | |
| 2012/0310328 A1 | 12/2012 | Olson et al. | |
| 2013/0035759 A1 | 2/2013 | Gross et al. | |
| 2013/0166022 A1 | 6/2013 | Conklin | |
| 2013/0172992 A1 | 7/2013 | Gross et al. | |
| 2013/0190865 A1 | 7/2013 | Anderson | |
| 2013/0211491 A1 | 8/2013 | Berreklouw | |
| 2013/0245753 A1 | 9/2013 | Alkhatib | |
| 2013/0317598 A1 | 11/2013 | Rowe et al. | |
| 2014/0005778 A1 | 1/2014 | Buchbinder et al. | |
| 2014/0046435 A1 | 2/2014 | Yeung et al. | |
| 2014/0207231 A1 | 7/2014 | Hacohen et al. | |
| 2014/0214160 A1 | 7/2014 | Naor | |
| 2014/0249622 A1 | 9/2014 | Carmi | |
| 2014/0277573 A1* | 9/2014 | Gill ....................... | A61F 2/2476 623/23.68 |
| 2014/0309680 A1 | 10/2014 | Fargahi | |
| 2014/0309727 A1 | 10/2014 | Lamelas | |
| 2014/0309730 A1 | 10/2014 | Alon | |
| 2014/0316513 A1 | 10/2014 | Tang | |
| 2014/0324164 A1 | 10/2014 | Gross et al. | |
| 2014/0350660 A1 | 11/2014 | Cocks et al. | |
| 2014/0358222 A1 | 12/2014 | Gorman, III et al. | |
| 2015/0112430 A1 | 4/2015 | Creaven et al. | |
| 2015/0119977 A1 | 4/2015 | Parodi et al. | |
| 2015/0327996 A1* | 11/2015 | Fahim ..................... | A61F 2/90 623/2.17 |

(56) References Cited

U.S. PATENT DOCUMENTS

2016/0081829 A1    3/2016  Rowe
2018/0000584 A1    1/2018  Duffy et al.

FOREIGN PATENT DOCUMENTS

| WO | WO2007130537 | 11/2007 |
| WO | WO2014081796 | 5/2014 |
| WO | WO2014080339 | 6/2014 |

* cited by examiner

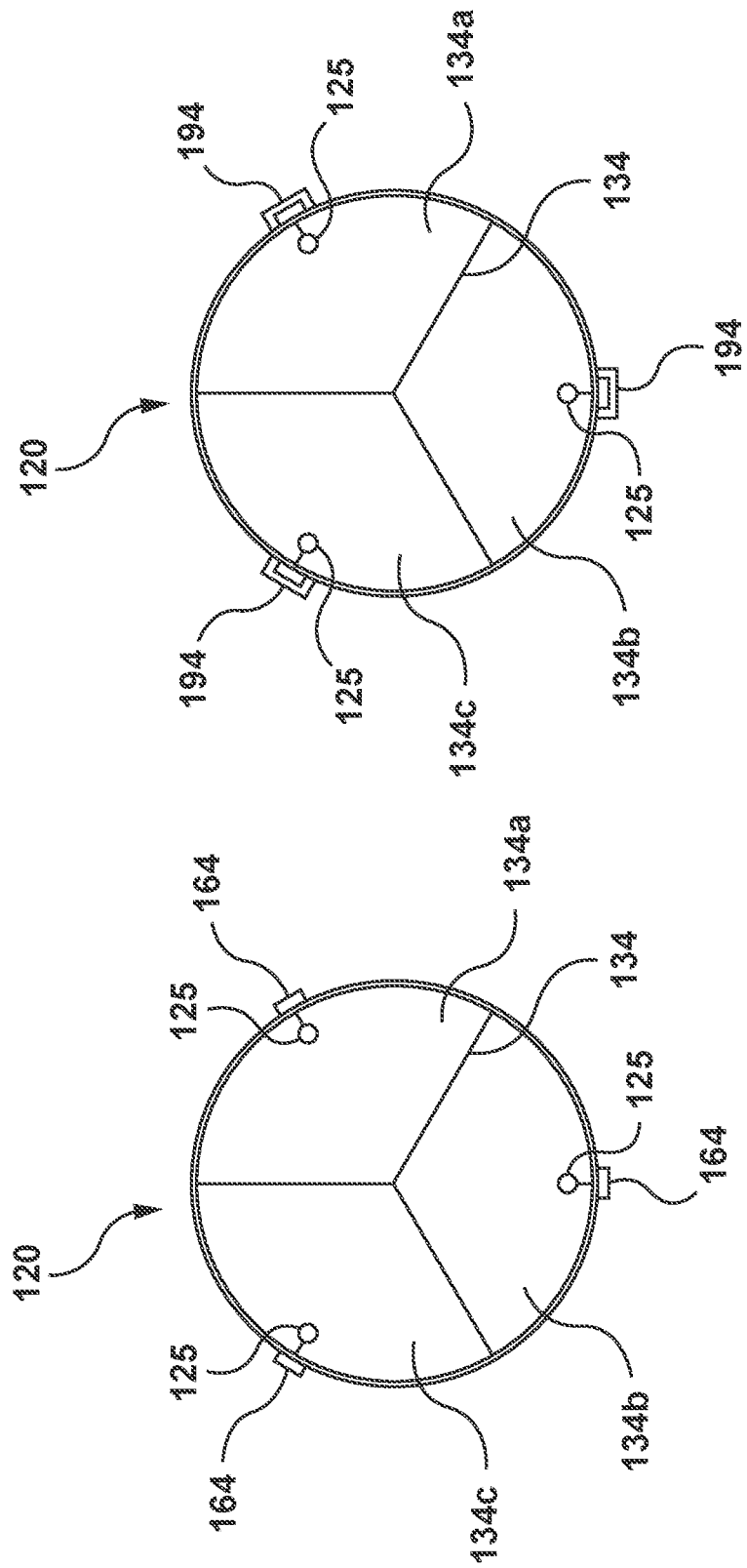

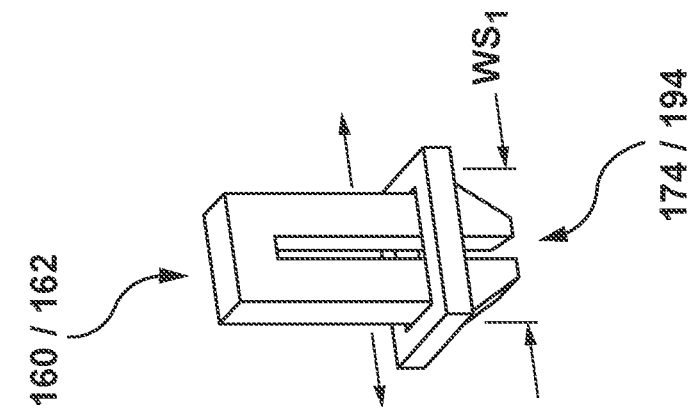
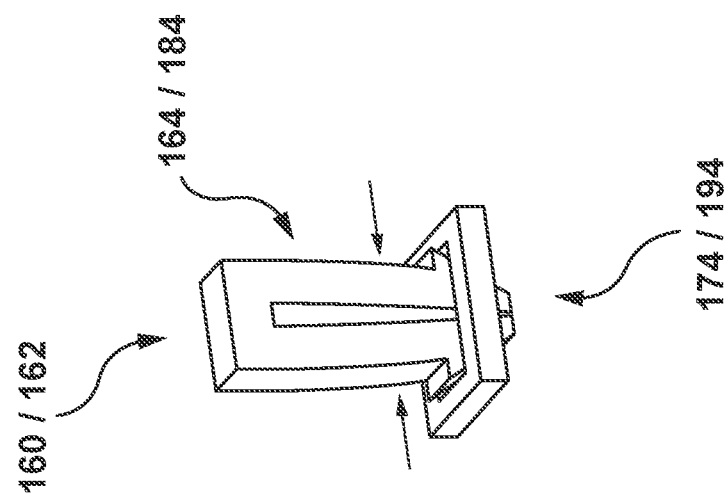
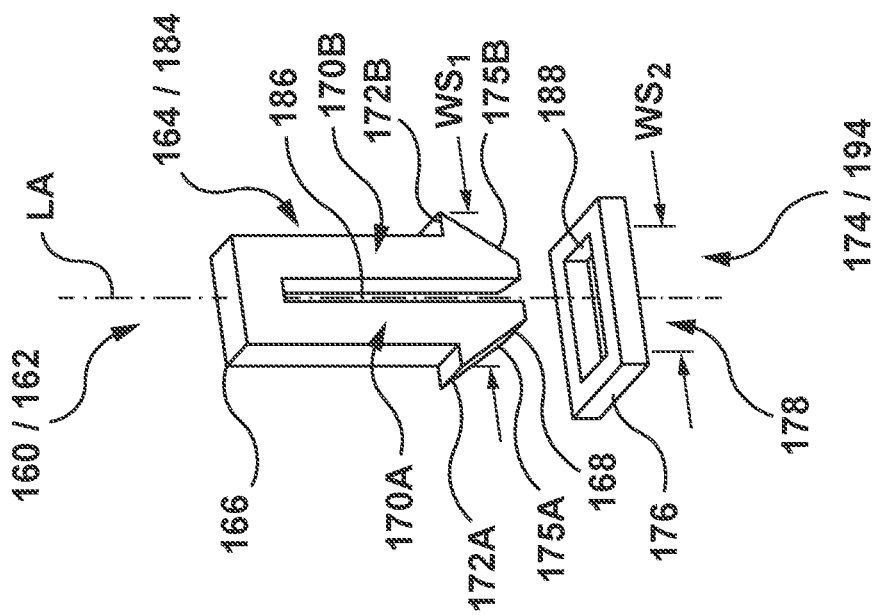

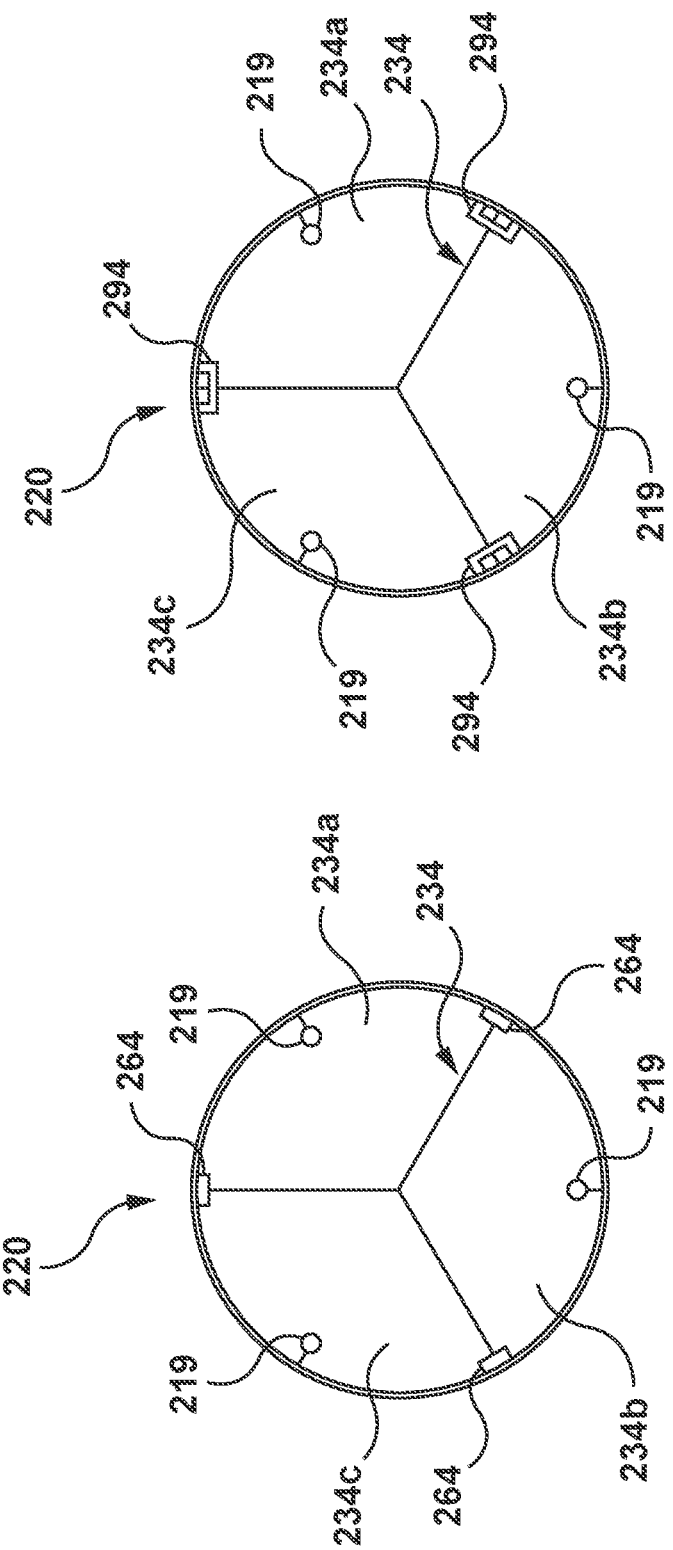

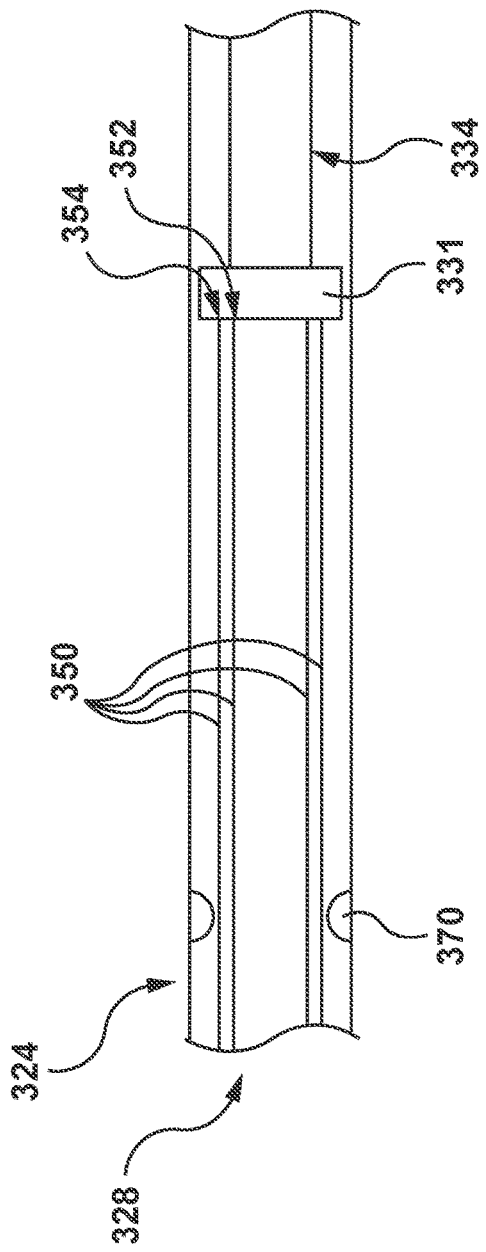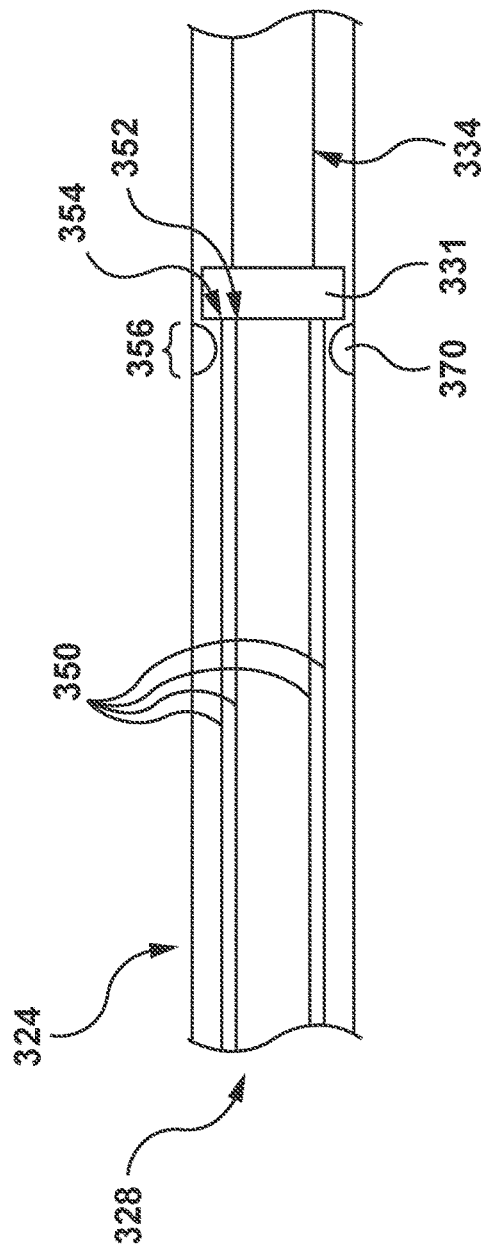

need for modular valve prostheses, delivery systems, and methods of guiding and aligning modules of such modular valve prostheses during deployment.

MODULAR VALVE PROSTHESIS, DELIVERY SYSTEM, AND METHOD OF DELIVERING AND DEPLOYING A MODULAR VALVE PROSTHESIS

CROSS-REFERENCE TO RELATED APPLICATION

This application is a divisional of U.S. patent application Ser. No. 15/186,593, filed Jun. 20, 2016, now allowed, the contents of which are incorporated herein by reference in their entirety.

FIELD OF THE INVENTION

The present invention relates to heart valve prostheses and methods for delivering and deploying heart valve prostheses. More particularly, the present invention relates to a modular valve prosthesis. The present invention also relates to a delivery device including a capsule with a plurality of sections and flexible bands between such sections.

BACKGROUND

Heart valves are sometimes damaged by disease or by aging, resulting in problems with the proper functioning of the valve. Heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery and implantation of replacement cardiac valves to solve the problems presented by traditional open surgery and minimally-invasive surgical methods. In such methods, a stented prosthetic heart valve, of valve prosthesis, is compacted for delivery in a catheter and then advanced, for example through an opening in the femoral artery, and through the descending aorta to the heart, where the valve prosthesis is then deployed in the valve annulus (e.g., the aortic valve annulus).

Various types and configurations of valve prostheses are available for percutaneous valve replacement procedures. In general, valve prosthesis designs attempt to replicate the function of the valve being replaced and thus will include valve leaflet-like structures. Valve prostheses are generally formed by attaching a bioprosthetic valve to a frame made of a wire or a network of wires. Such a stented prosthetic heart valve can be compressed radially to introduce the stented prosthetic heart valve into the body of the patient percutaneously through a catheter. The stented prosthetic heart valve may be deployed by radially expanding it once positioned at the desired treatment site.

Often, the ability to traverse the tortuous vasculature prior to reaching the treatment site is limited by the state of the disease and/or varying anatomical size of the vasculature.

Accordingly, there is a need for valve prostheses and delivery systems for valve prostheses that are sufficiently flexible to navigate tortuous vessel. In particular, there is a need for modular valve prostheses, delivery systems, and methods of guiding and aligning modules of such modular valve prostheses during deployment.

SUMMARY OF THE INVENTION

Embodiments hereof relate to a modular valve prosthesis including an inflow stent, a valve component, and an outflow stent. The modular valve prosthesis includes a radially collapsed delivery configuration and a radially expanded deployed configuration. The inflows stent includes an inflow end and an outflow end. The valve component includes a valve stent and a prosthetic valve coupled to the valve stent such that the prosthetic valve is disposed in an interior lumen of the valve stent. The valve stent includes an inflow end and an outflow end. The inflow end of the valve stent faces the outflow end of the inflow stent. The outflow stent includes an inflow end and an outflow end. The inflow end of the outflow stent faces the outflow end of the valve stent. When the modular valve prosthesis is in the radially collapsed delivery configuration, the inflow end of the valve stent is not in contact with the outflow end of the inflow stent and the outflow end of the valve stent is not in contact with the inflow end of the outflow stent. When the modular valve prosthesis is in the radially expanded deployed configuration, the inflow end of the valve stent is in contact with the outflow end of the inflow stent and the outflow end of the valve stent is in contact with the inflow end of the outflow stent.

Embodiments hereof also relate to a delivery system for delivering a modular valve prosthesis including an outer sheath surrounding an inner shaft. The outer sheath includes a capsule at a distal portion thereof. The capsule is configured to maintain the modular valve prosthesis in a radially compressed delivery configuration for delivery to a treatment site. The capsule is configured to be retracted to release the modular valve prosthesis at the treatment site. The capsule includes a first section and a second section. The first section and the second section are aligned with corresponding first and second modules of the modular valve prosthesis when the modular valve prosthesis is in the radially compressed delivery configuration. The capsule includes a first band between the first section and the second section, and the first band is configured to be aligned with a first gap between the first module and the second module of the modular valve prosthesis when the modular valve prosthesis is in the radially compressed delivery configuration. The first band is more flexible than each of the first section and the second section.

Embodiments hereof also relate to a method for delivering and deploying a modular valve prosthesis. The method includes manipulating a delivery system loaded with the modular valve prosthesis in a radially compressed delivery configuration through a patient's vasculature to a treatment site. The modular valve prosthesis includes an inflow stent, a valve component, and an outflow stent. The delivery system includes an outer sheath including a capsule. The capsule includes a first section, a second section, a third section, a first band disposed between the first section and the second section, and a second band disposed between the second section and the third section. The modular valve prosthesis is loaded within the capsule with the inflow stent aligned with the first section, a first gap between the inflow stent and the valve component aligned with the first band, the valve component aligned with the second section, a second gap between the valve component and the outflow stent aligned with the second band, and the outflow stent aligned with third section. The delivery system further includes a plurality of sutures coupled to a hub and extending through each of the inflow stent, the valve component, and the outflow stent. The method includes retracting the capsule such that the inflow stent is released from the capsule and transitions from the radially compressed delivery configuration to a radially expanded deployed configuration. The method further includes retracting the hub such that the sutures are taut. The method further includes further retracting the capsule such that the valve component is released from the capsule. The valve component transitions from the radially compressed delivery configuration to the radially expanded deployed configuration and couples with the inflow stent. The method further includes retracting the hub such that the sutures are taut. The method further includes further retracting the hub to release the outflow stent from the capsule. The outflow stent transitions from the radially compressed delivery configuration to the radially expanded deployed configuration and couples with the valve component.

BRIEF DESCRIPTION OF DRAWINGS

FIG. 4A is an end illustration of the inflow end of the valve component of FIG. 1.

FIG. 4B is an end illustration of the outflow end of the valve component of FIG. 1.

FIG. 6A is a close-up perspective illustration of an embodiment of a locking mechanism of the modular valve prosthesis of FIG. 1 in an unlocked configuration.

FIG. 6B is a close-up perspective illustration of the locking mechanism of FIG. 6A in a compressed configuration.

FIG. 6C is a close-up perspective illustration of the locking mechanism of FIG. 6A in a locked configuration.

FIG. 10A is an end illustration of the inflow end of the valve component of FIG. 7.

FIG. 10B is an end illustration of the outflow end of the valve component of FIG. 7.

FIGS. 16A and 16B are close-up illustrations of a suture detaching mechanism of the delivery system of FIG. 13.

DETAILED DESCRIPTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the clinician and "proximal" and "proximally" refer to positions near, or in a direction toward the clinician. When the terms "distal" and "proximal" are used in the following description to refer to a device to be implanted into a native artery, such as a modular valve prosthesis, they are used with reference to the direction of blood flow from the heart. Thus "distal" and "distally" refer to positions in a downstream direction with respect to the direction of blood flow and "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

In general terms, the modular valve prosthesis of the present disclosure includes an inflow stent, a valve component, and an outflow stent. The modular valve prosthesis includes a radially compressed delivery configuration for delivery to a treatment site and a radially expanded deployed configuration when deployed at the treatment site. The modular valve prosthesis is configured to be delivered to the treatment site as separate modules (unassembled), and assembled at the treatment site.

Figure 1:
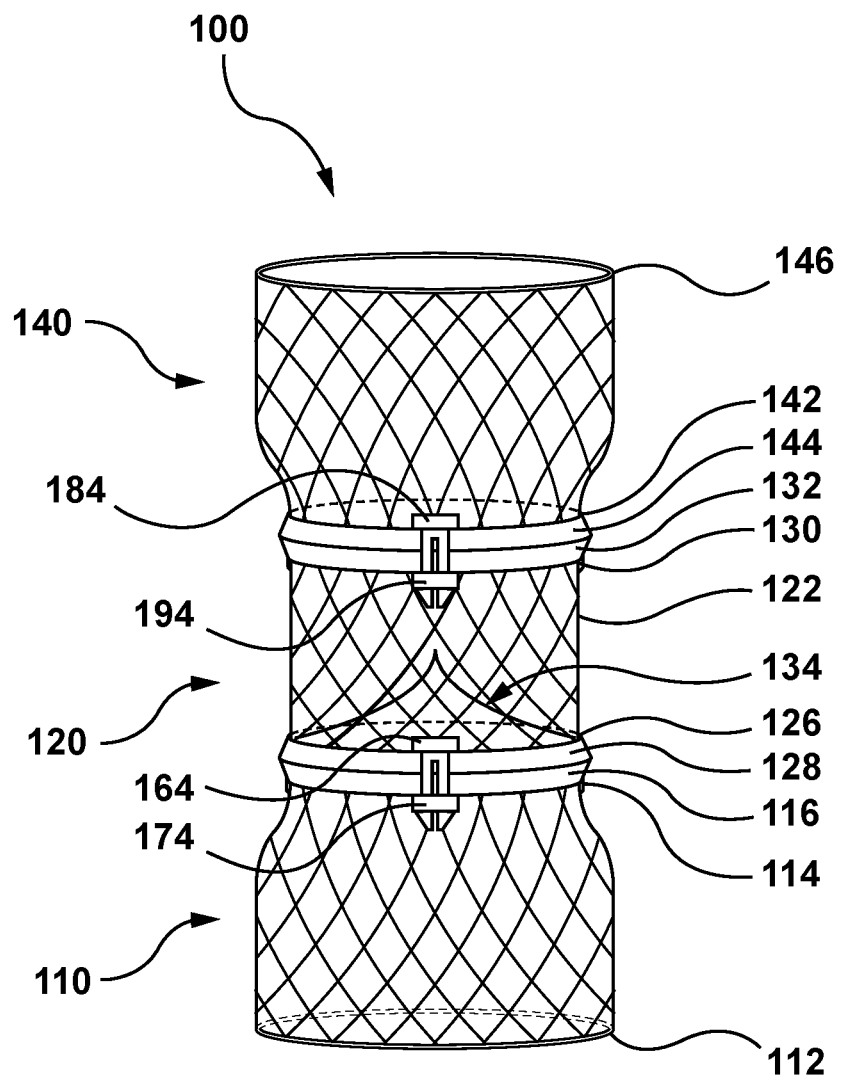
FIG. 1 is a perspective illustration of an embodiment of a modular valve prosthesis according to an embodiment hereof, wherein the modular valve prosthesis is in a radially expanded deployed configuration.

With the above understanding in mind, a modular valve prosthesis 100 according to an embodiment of the present invention is shown in FIGS. 1-7C. Modular valve prosthesis 100 includes a first or inflow stent 110, a valve component 120, and a third or outflow stent 140, as shown in FIG. 1. In an embodiment, modular valve prosthesis 100 further includes a plurality of first locking mechanisms 160 for coupling inflow stent 110 and valve component 120 together, and a plurality of second locking mechanism 162 for coupling valve component 120 and outflow stent 140 together, as described in more detail below. Modular valve prosthesis 100 includes a radially compressed delivery configuration (not shown) for delivery to the treatment site of a native valve and a radially expanded deployed configuration, as shown in FIG. 1. Modular valve prosthesis 100 may be self-expanding or balloon expandable based upon the application. Components in accordance with the embodiment of modular valve prosthesis 100 of FIG. 1 are presented in greater detail in FIGS. 2-6C. Various features of the components of modular valve prosthesis 100 reflected in FIGS. 1-6C and described below can be modified or replaced with differing structures and/or mechanisms. Modular valve prosthesis 100, described in greater detail below, is merely an exemplary embodiment of a percutaneous modular valve prosthesis according to an embodiment hereof and modifications can be made to the embodiments described herein, without departing from the spirit and scope of the present invention. The present disclosure is in no way limited to inflow stent 110, valve component 120, and outflow stent 140 shown and described below. Components of modular valve prosthesis 100 may assume different forms and construction based upon application needs as described in greater detail in for example, U.S. Pat. No. 8,226,710 to Nguyen incorporated in its entirety by reference herein. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Inflow stent 110, as shown in FIGS. 1-3B, is of a generally tubular configuration, and includes a radially compressed delivery configuration and a radially expanded deployed configuration. Inflow stent 110 includes an inflow end 112 and an outflow end 114, and defines an inflow lumen 118 therein. Inflow stent 110 further includes a plurality of suture guides 119, and a plurality of lock loops 174 corresponding to first locking mechanisms 160. Inflow stent 110 further includes an outflow flange 116.

Figure 3B:
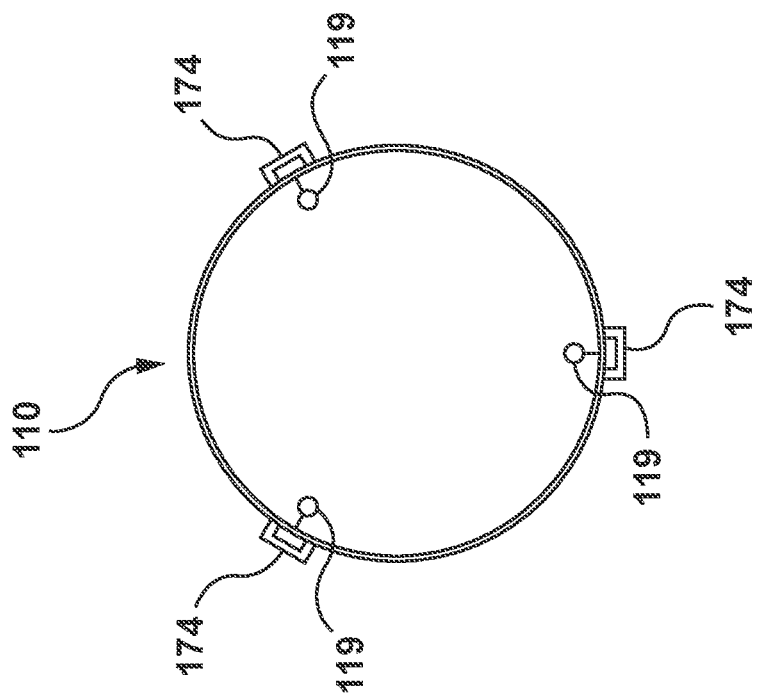
FIG. 3B is an end illustration of the outflow end of the inflow stent of FIG. 1.
Figure 3A:
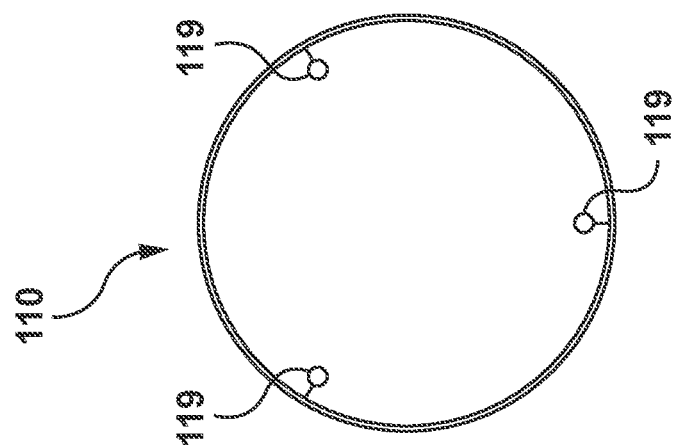
FIG. 3A is an end illustration of the inflow end of the inflow stent of FIG. 1.

In an embodiment, suture guides 119 are disposed about an interior circumference of inflow stent 110, extending into inflow lumen 118, as shown in FIGS. 3A-3B. In an embodiment, a set of suture guides 119 is disposed at inflow end 112 of inflow stent 110, as shown in FIG. 3A, and a set of suture guides 119 is disposed at outflow end 114 of inflow stent 110, as shown in FIG. 3B. Suture guides 119 are configured to retain sutures 150, described below, therethrough. More particularly, suture guides 119 provide routing of sutures 150 through inflow stent 110. Suture guides 119 may be configured, for example, and not by way of limitation, as rings, hooks, loops, or any other configuration suitable for purposes of the present disclosure. In an embodiment, there are three (3) suture guides 119 at the inflow end 112 and the outflow end 114. However, more or fewer suture guides 119 may be used. They also need not be located at the ends of inflow stent 110, as shown.

In an embodiment, lock loops 174 of first locking mechanisms 160 are disposed about an exterior circumference of inflow stent 110 at outflow end 114 of inflow stent 110, as shown in FIG. 3B. More particularly, lock loops 174 of first locking mechanisms 160 are configured to couple to a plurality of corresponding lock portions 164 of first locking mechanisms 160 to couple inflow stent 110 to valve stent 122, as described in greater detail below. In an embodiment, there are three (3) lock loops 174 spaced equally circumferentially about inflow stent 110. However, more or fewer lock loops 174 may be used and they need not be equally spaced.

Outflow flange 116 is disposed at outflow end 114 of inflow stent 110. More particularly, outflow flange 116 of inflow stent 110 is configured to abut a corresponding inflow flange 128 of valve component 120 when in the radially expanded deployed configuration, as shown in FIG. 1. When abutting against corresponding inflow flange 128 of valve stent 122, outflow flange 128 aids in sealing inflow stent 110 to valve stent 122. Outflow flange 114 of inflow stent 110 may be formed, for example, and not by way of limitation, of silicone, fabric, polyester, rubber based materials, tissue/pericardium, and/or a foam/open cell structure.

Inflow stent 110 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

Valve component 120 is of a generally tubular configuration, is disposed distally or downstream of inflow stent 110, and includes a radially compressed delivery configuration and a radially expanded deployed configuration. Valve component 120 includes a second or valve stent 122 and a prosthetic valve 134. Valve stent 122 includes an inflow end 126 and an outflow end 130, and defines a valve lumen 124 therein. Valve stent 122 further includes a plurality of suture guides 125, a plurality of lock portions 164 corresponding to first locking mechanisms 160, a plurality of lock loops 194 corresponding to second locking mechanisms 162, an inflow flange 128, and an outflow flange 132, as shown in FIGS. 1-2 and FIGS. 4A-4B.

In an embodiment, suture guides 125 are disposed about an interior circumference of valve stent 122, extending into valve lumen 124. In an embodiment, a set of suture guides 125 is disposed at inflow end 126 of valve stent 122, as shown in FIG. 4A, and a set of suture guides 125 is disposed at outflow end 130 of valve stent 122, as shown in FIG. 4B. Suture guides 125 are configured to retain sutures 150, described below, therethrough. More particularly, suture guides 125 provide routing of sutures 150 through valve stent 122 and alignment of valve component 120 relative to inflow stent 110, as described in greater detail below. Suture guides 125 may be configured, for example, and not by way of limitation, as rings, hooks, loops, or any other configuration suitable for purposes of the present disclosure. In an embodiment, there are three (3) suture guides 125 at each of the inflow end 126 and the outflow end 130. However, more or fewer suture guides 125 may be used. Further, they may be disposed other than at the inflow and outflow ends of valve stent 122

Figure 2:
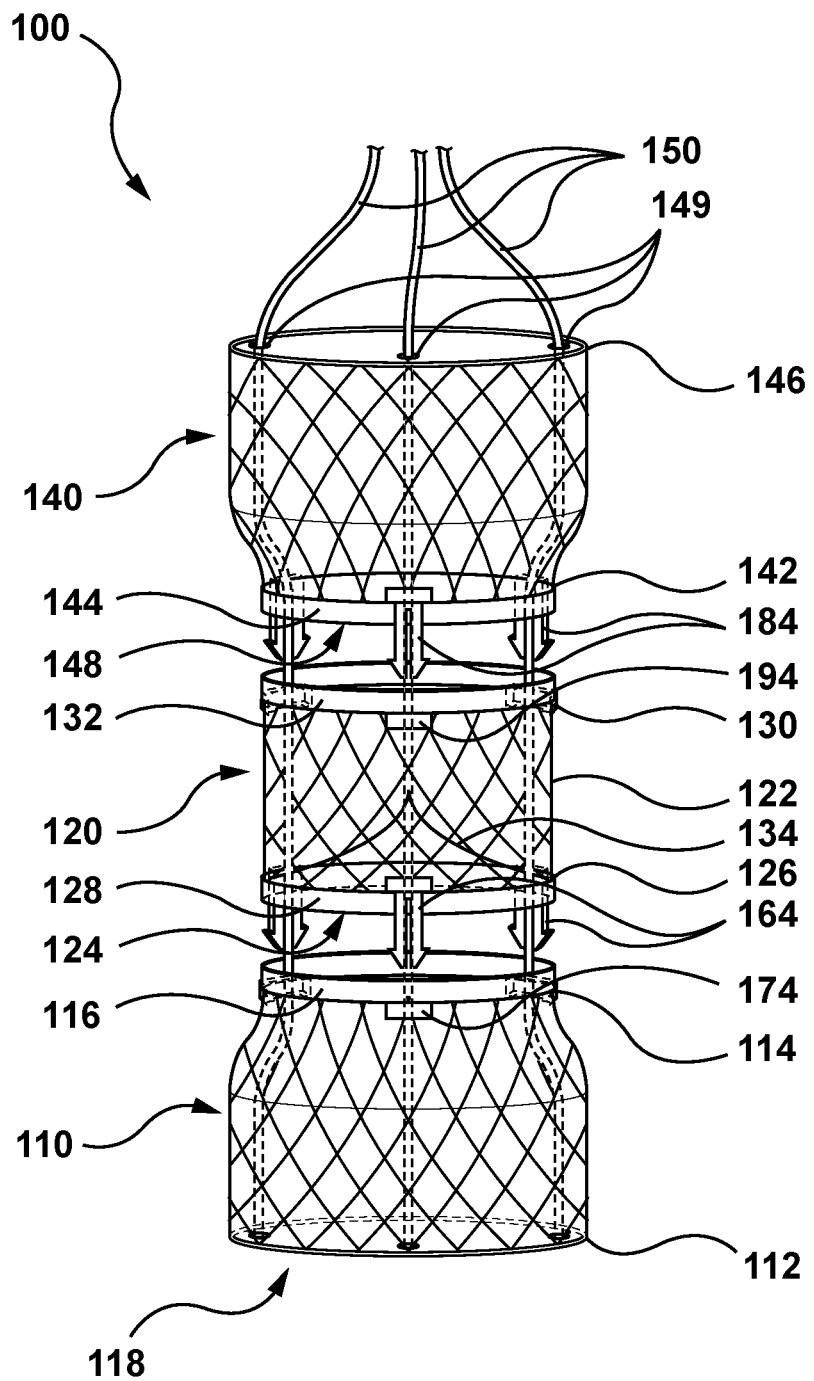
FIG. 2 is a perspective illustration of the modular valve prosthesis of FIG. 1 in a radially expanded deployed configuration, with the modules separated for viewing clarity.

In an embodiment, lock portions 164 of first locking mechanisms 160 are disposed about an exterior circumference of valve stent 122 at inflow end 126, as shown in FIGS. 2 and 4A. More particularly, lock portions 164 of first locking mechanisms 160 are configured to couple to corresponding lock loops 174 of first locking mechanisms 160 in order to couple valve stent 122 to inflow stent 110, as described in greater detail below. In an embodiment, there are three (3) lock portions 164 spaced equally circumferentially about valve stent 122. However, more or fewer lock portions 164 may be used and they need not be equally spaced.

In an embodiment, lock loops 194 of second locking mechanisms 162 are disposed about the exterior circumference of valve stent 122 at outflow end 130, as shown in FIGS. 2 and 4B and described in greater detail below. More particularly, lock loops 194 of second locking mechanisms 162 are configured to couple to corresponding lock portions 184 of second locking mechanisms 162 in order to couple valve stent 122 to outflow stent 140, as described in greater detail below. In an embodiment, there are three (3) lock loops 194 spaced equally circumferentially about valve stent 122. However, more or fewer lock loops 194 may be used and they need not be equally spaced.

Inflow flange 128 is disposed at inflow end 126 of valve stent 122 and outflow flange 132 is disposed at outflow end 130 of valve stent 122. More particularly, inflow flange 128 of valve stent 122 is configured to abut with corresponding outflow flange 116 of inflow stent 110 and outflow flange 132 of valve stent 122 is configured to abut with a corresponding inflow flange 144 of outflow stent 140 when in the radially expanded deployed configuration, as shown in FIG. 1. When abutting against corresponding flanges 116/144, flanges 128/132 aid in sealing valve stent 122 to inflow stent 110 and outflow stent 140, respectively. Flanges 128/132 of valve stent 122 may be formed, for example, and not by way of limitation, of silicone, fabric, polyester, rubber based materials, tissue/pericardium, and/or a foam/open cell structure.

Prosthetic valve 134 is disposed within interior lumen 124 of valve stent 122, as shown in FIGS. 1-2 and can assume a variety of configurations described in greater detail in for example, U.S. Pat. No. 8,226,710 to Nguyen, previously incorporated herein. In an embodiment, as shown in FIGS. 4A-4B, prosthetic valve 134 comprises three (3) leaflets 134a, 134b, 134c. However, more or fewer leaflets, such as a bi-leaflet design, may be utilized.

Valve stent 122 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure. Prosthetic valve 134 may be formed of materials as are known in the art.

Outflow stent 140 is of a generally tubular configuration, and includes a radially compressed delivery configuration and a radially expanded deployed configuration. Outflow stent 140 includes an inflow end 142 and an outflow end 146, and defines an outflow lumen 148 therein. Outflow stent 140 further includes a plurality of suture guides 149, a plurality of lock portions 184 of second locking mechanisms 162, and an inflow flange 144, as shown in FIGS. 1-2 and FIGS. 5A-5B.

Figure 5B:
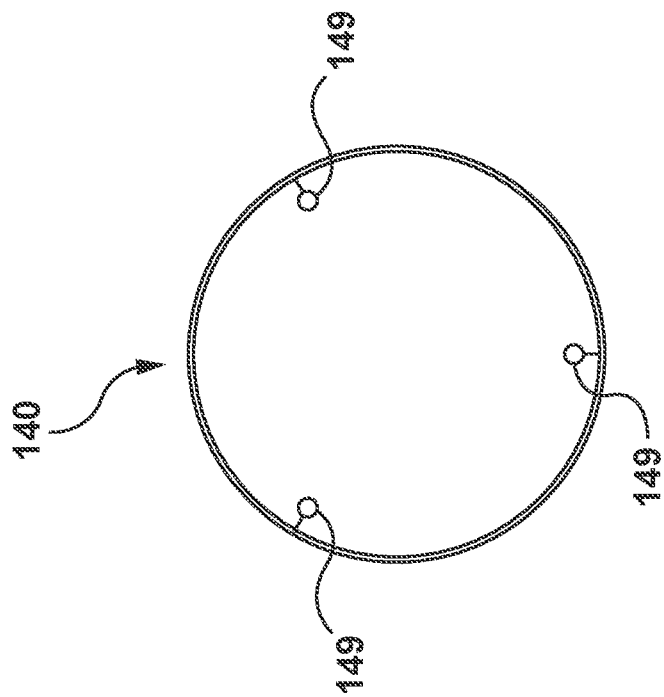
FIG. 5B is an end illustration of the outflow end of the outflow stent of FIG. 1.
Figure 5A:
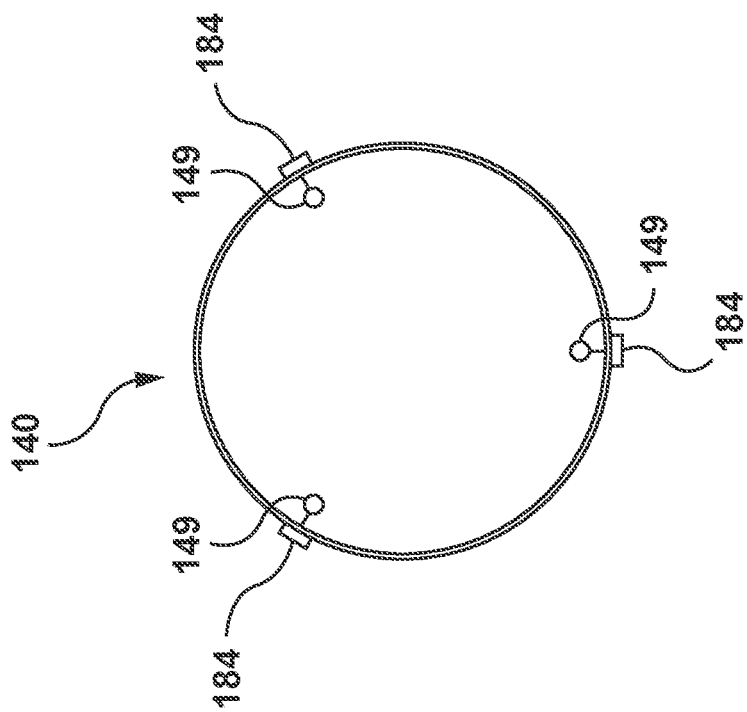
FIG. 5A is an end illustration of the inflow end of the outflow stent of FIG. 1.

In an embodiment, suture guides 149 are disposed about an interior circumference of outflow stent 140, as shown in FIGS. 5A-5B. In an embodiment, a set of suture guides 149 is disposed at inflow end 142 of outflow stent 140, as shown in FIG. 5A, and a set of suture guides 149 is disposed at outflow end 146 of outflow stent 140, as shown in FIG. 5B. Suture guides 149 are configured to retain sutures 150, described below, therethrough. More particularly, suture guides 149 provide routing of sutures 150 through outflow stent 140 and alignment of outflow stent 140 relative to valve component 120 and inflow stent 110. Suture guides 149 may be configured, for example, and not by way of limitation, as rings, hooks, loops, or any other configuration suitable for purposes of the present disclosure. In an embodiment, there are three (3) suture guides 149 at each of the inflow end 142 and the outflow end 146. However, more or fewer suture guides 149 may be used. Further, they need not be disposed at the inflow and outflow ends of outflow stent 140.

In an embodiment, lock portions 184 of second locking mechanisms 162 are disposed about the exterior circumference of outflow stent 140 at inflow end 142, as shown in FIG. 5A. More particularly, lock portions 184 of second locking mechanisms 162 are configured to couple to corresponding lock loops 194 of second locking mechanisms 162 to couple outflow stent 140 to valve stent 122, as described in greater detail below.

Inflow flange 144 is disposed at inflow end 142 of outflow stent 140. More particularly, inflow flange 144 of outflow stent 140 is configured to abut with corresponding outflow flange 132 of valve stent 122 of valve component 120 when in the radially expanded deployed configuration, as shown in FIG. 1. When abutting against corresponding outflow flange 132 of valve stent 122, inflow flange 144 and outflow flange 132 aid in sealing outflow stent 140 to valve stent 122. Inflow flange 144 of outflow stent 140 may be formed, for example, and not by way of limitation, of silicone, fabric, polyester, rubber based materials, tissue/pericardium, and/or a foam/open cell structure.

Outflow stent 140 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

As explained above, a set of first locking mechanisms 160 couple inflow stent 110 to valve stent 122, and a set of second locking mechanisms 162 couple valve stent 122 to outflow stent 140. In an embodiment, first locking mechanisms 160 and second locking mechanisms are disposed about the exterior circumference of respective inflow stent 110, valve component 120, and outflow stent 140 of modular valve prosthesis 100, as previously described. First locking mechanisms 160 and second locking mechanisms 162 include an unlocked configuration, a compressed configuration, and a locked configuration. As explained above, and shown in more detail in FIGS. 6A-6C, first locking mechanisms 160 and second locking mechanisms 162 include lock portions 164/184 and lock loops 174/194, respectively. In an embodiment, lock portions 164/184 include a pair of legs 170A/170B disposed between a proximal end 166 and a distal end 168. Legs 170A/170B are joined adjacent proximal end 166. A gap 186 separates first leg 170A and second leg 170B distal of where they are joined. First leg 170A and second leg 170B each include a shoulder 172A/172B extending from an outer surface thereof outwardly relative to a longitudinal axis LA of lock portion 164/184. Distal of shoulders 172A/172B, each leg includes a ramp 175A/175B such that the outer surface tapers back toward the longitudinal axis LA towards distal end 168. Lock loops 174/194 include a frame loop 176 defining a loop lumen 178 therein.

Lock portions 164/184 and lock loops 174/194 are configured such that a static width $WS_1$ at shoulders 172A/172B is greater than a static width $WS_2$ of lock lumen 178 of lock loops 174/194, as shown in FIG. 6A. Lock portions 164/184 and lock loops 174/194 are further configured such that distal end 168 of lock portion 164/184 fits within loop lumen 178. As lock portion 164/184 is advanced through lock loop 174/194, or lock loop 174/194 is advanced over lock portion 164/184, ramps 175A/175B of legs 170A/170B contact an inner surface 188 of lock loop 174/194 defining loop lumen 178. As lock portion 164/184 continues to advance through loop lumen 178, pressure of inner surface 188 against ramps 175A/175B compress legs 170A/170B towards each other, reducing gap 186, as shown in FIG. 6B, such that shoulders 172A/172B may traverse loop lumen 178 of lock loop

174/194. Lock portions 164/184 and lock loops 174/194 are further configured such that once shoulders 172A/17B traverse loop lumen 178, legs 170A/170B move away from each other, as shown in FIG. 6C. Shoulders 172A/172B prevent lock loop 174/194 from moving distally relative to lock portion 164/184. Lock portions 164/184 and lock loops 174/174 may be formed, for example, and not by way of limitation, of stainless steel, Nitinol, nylon, polybutester, polypropylene, polyester or other materials suitable for the purposes described herein. FIGS. 6A-6C show one example of first and second locking mechanisms 160/162. Those skilled in the art would recognize that other locking mechanisms suitable for purposes of the present disclosure may be utilized. For example, and not by way of limitation, the locking mechanism described with respect to FIGS. 12A-12C below may be utilized.

According to embodiments hereof, valve component 120 is configured to be disposed at outflow end 114 of inflow stent 110 and outflow stent 140 is configured to be disposed at outflow end 130 of valve stent 122 of valve component 120, as shown in FIG. 1. More particularly, inflow flange 128 of valve stent 122 of valve component 120 is configured to contact outflow flange 116 of inflow stent 110, and inflow flange 144 of outflow stent 140 is configured to contact outflow flange 132 of valve stent 122 of valve component 120 when in the radially expanded deployed configuration. Stated another way, when modular valve prosthesis 100 is in the radially expanded deployed configuration, outflow flange 116 is in contact with inflow flange 128, and outflow flange 132 is in contact with inflow flange 144. Outward radial forces of inflow stent 110, valve component 120, and outflow stent 140 imparted against walls at the native valve when the modular valve prosthesis 100 is in the radially expanded deployed configuration maintains positioning of modular valve prosthesis 100 within the affected valve and maintains contact of inflow flange 128 of valve stent 122 of valve component 120 with outflow flange 116 of inflow stent 110, and outflow flange 132 of valve stent 122 of valve component 120 with inflow flange 144 of outflow stent 140.

FIGS. 1 and 2 also show sutures 150 disposed through the interior of inflow stent 110, valve component 120, and outflow stent 140 of modular valve prosthesis 100. Sutures 150 are shown in FIG. 2 with modular valve prosthesis 100 in the radially expanded deployed configuration with the modules thereof separated for clarity and explanation purposes only. Sutures 150 are coupled to a delivery system, as described below, and disposed within/through suture guides 119 of inflow stent 110, suture guides 125 of valve component 120, and suture guides 149 of outflow stent 140 when in the radially compressed delivery configuration such that inflow stent 110, valve component 120, and outflow stent 140 may be properly aligned at a treatment site upon deployment thereof, as shown in FIGS. 1-2 and described in greater detail below. Sutures 150 are configured such that sutures 150 radially and longitudinally align valve component 120 with inflow stent 110 and radially and longitudinally align outflow stent 140 with valve component 120. Sutures 150 may be formed, for example, and not by way of limitation, of stainless steel, Nitinol, nylon, polybutester, polypropylene, silk, polyester or other materials suitable for the purposes described herein.

Figure 7:
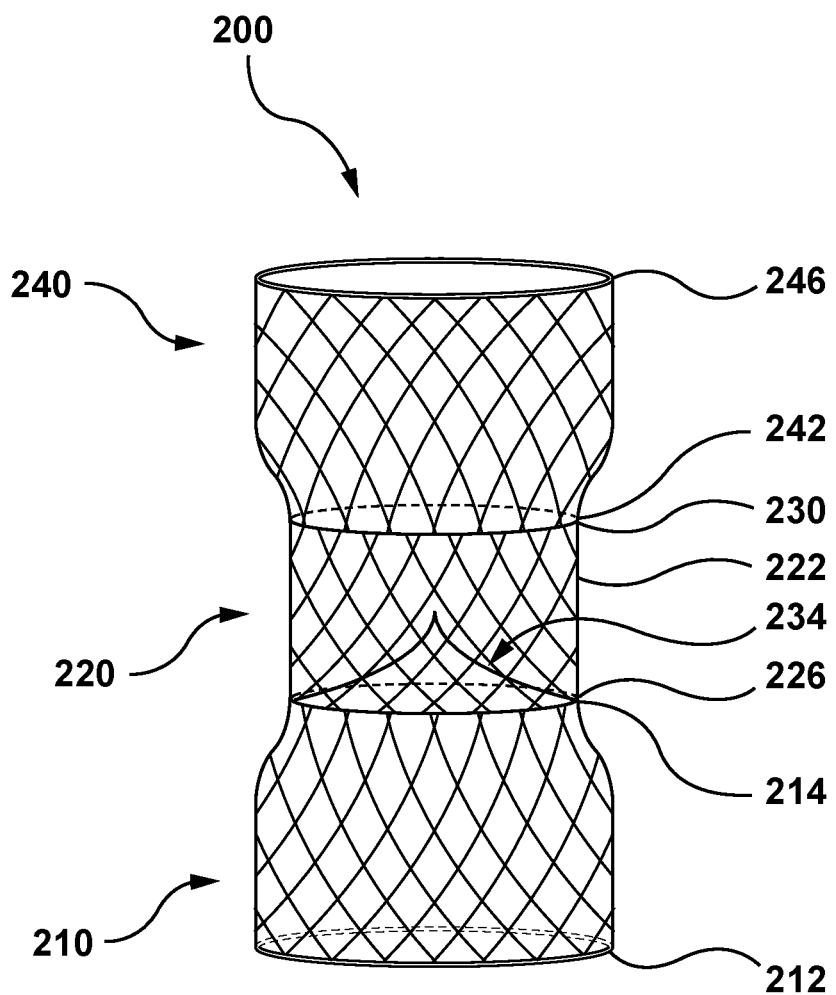
FIG. 7 is a perspective illustration of a modular valve prosthesis according to another embodiment hereof.

A modular valve prosthesis 200 according to another embodiment of the present invention is shown in FIGS. 7-12C. Modular valve prosthesis 200 includes a first or inflow stent 210, a valve component 220, and a third or outflow stent 240, as shown in FIG. 7. In an embodiment, modular valve prosthesis 200 further includes a plurality of first locking mechanisms 260 for coupling inflow stent 210 and valve component 220 together, and a plurality of second locking mechanisms 262 for coupling valve component 220 and outflow stent 240 together, as described in more detail below. Modular valve prosthesis 200 includes a radially compressed delivery configuration (not shown) for delivery to the treatment site of a native valve and a radially expanded deployed configuration, as shown in FIG. 7. Modular valve prosthesis 200 may be self-expanding or balloon expandable based upon the application. Components in accordance with the embodiment of modular valve prosthesis 200 of FIG. 7 are presented in greater detail in FIGS. 8-12C. Various features of the components of modular valve prosthesis 200 reflected in FIGS. 7-12C and described below can be modified or replaced with differing structures and/or mechanisms. Modular valve prosthesis 200, described in greater detail below, is merely an exemplary embodiment of a percutaneous modular valve prosthesis according to an embodiment hereof and modifications can be made to the embodiments described herein, without departing from the spirit and scope of the present invention. The present disclosure is in no way limited to inflow stent 210, valve component 220, and outflow stent 240 shown and described below. Components of modular valve prosthesis 200 may assume different forms and construction based upon application needs as described in greater detail in for example, U.S. Pat. No. 8,226,710 to Nguyen incorporated in its entirety by reference herein. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

In an embodiment, inflow stent 210, as shown in FIGS. 7-9C, is of a generally tubular configuration, and includes a radially compressed delivery configuration and a radially expanded deployed configuration. Inflow stent 210 includes an inflow end 212 and an outflow end 214, and defines an inflow lumen 218 therein. Inflow stent 210 further includes a plurality of suture guides 219, and a plurality of lock loops 274 corresponding to first locking mechanisms 260.

Figure 9B:
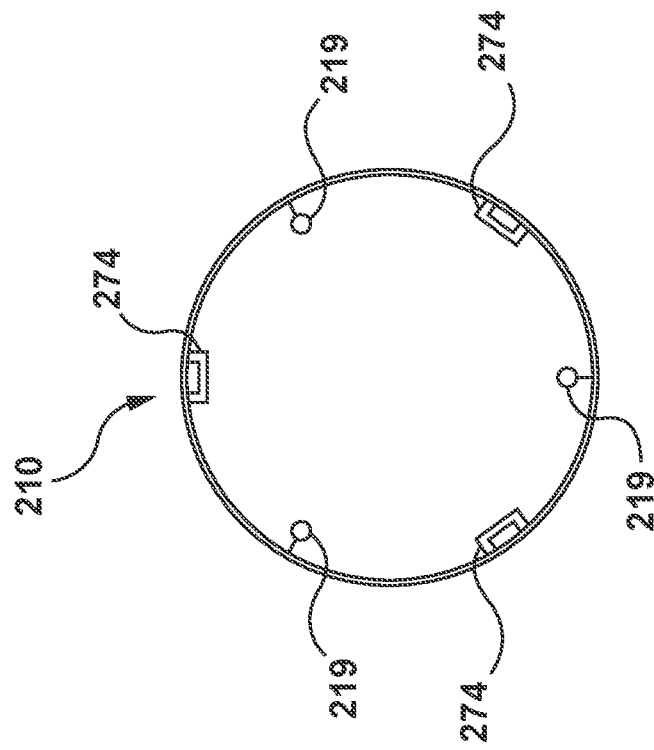
FIG. 9B is an end illustration of the outflow end of the inflow stent of FIG. 7.
Figure 9A:
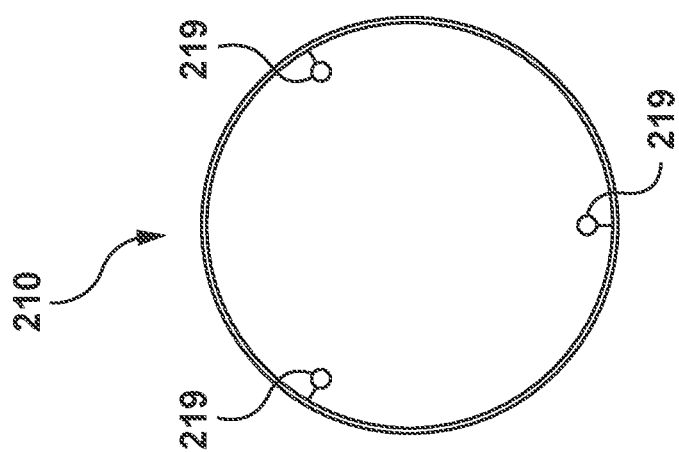
FIG. 9A is an end illustration of the inflow end of the inflow stent of FIG. 7.

In an embodiment, suture guides 219 are disposed about an interior circumference of inflow stent 210, as shown in FIGS. 9A-9B. In an embodiment, a set of suture guides 219 is disposed at inflow end 212 of inflow stent 210, as shown in FIG. 9A, and a set of suture guides 219 is disposed at outflow end 214 of inflow stent 210, as shown in FIG. 9B. Suture guides 219 are configured to retain sutures 250, described below, therethrough. More particularly, suture guides 219 provide routing of sutures 250 through inflow stent 210. Suture guides 219 may be configured, for example, and not by way of limitation, as rings, hooks, loops, or any other configuration suitable for purposes of the present disclosure. In an embodiment, there are three (3) suture guides 219 at the inflow end 212 and the outflow end 214. However, more or fewer suture guides 219 may be used. Further, they need not be located at the inflow and outflow ends of inflow stent 210.

In an embodiment, lock loops 274 of first locking mechanisms 260 are disposed about the interior circumference of inflow stent 210, extending into inflow lumen 218, at outflow end 214 of inflow stent 210, as shown in FIG. 9B. More particularly, lock loops 274 of first locking mechanisms 260 are configured to couple to a plurality of corresponding lock portions 264 of first locking mechanisms 260 to couple inflow stent 210 to valve stent 212, as described in greater detail below. In an embodiment, there are three (3) lock loops 174 spaced equally circumferentially about inflow stent 110. However, more or fewer lock loops 174 may be used and they need not be equally spaced.

Outflow end 214 of inflow stent 210 is configured to be connected to a corresponding inflow end 226 of valve stent 222 of valve component 220 when in the radially expanded deployed configuration, as shown in FIG. 7. Inflow stent 210 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

Valve component 220 is of a generally tubular configuration, is disposed distally of inflow stent 210, and includes a radially compressed delivery configuration and a radially expanded deployed configuration. Valve component 220 includes a valve stent 222 and a prosthetic valve 234. Valve stent 222 includes an inflow end 226 and an outflow end 230, and defines a valve lumen 124 therein. Valve stent 222 further includes a plurality of suture guides 225, a plurality of lock portions 264 corresponding to first locking mechanisms 260, and a plurality of lock portions 284 corresponding to second locking mechanisms 262, as shown in FIGS. 7-8 and FIGS. 10A-10B.

In an embodiment, suture guides 225 are disposed about an interior circumference of valve stent 222, extending into valve lumen 224. In an embodiment, a set of suture guides 225 is disposed at inflow end 226 of valve stent 122, as shown in FIG. 10A, and a set of suture guides 225 is disposed at outflow end 230 of valve stent 222, as shown in FIG. 10B. Suture guides 225 are configured to retain sutures 250, described below, therethrough. More particularly, suture guides 225 provide routing of sutures 250 through valve stent 222 and alignment of valve component 220 relative to inflow stent 210 and outflow stent 240, as described in greater detail below. Suture guides 225 may be configured, for example, and not by way of limitation, as rings, hooks, loops, or any other configuration suitable for purposes of the present disclosure. In an embodiment, there are three (3) suture guides 225 at each of the inflow end 226 and the outflow end 230 spaced equally around an inner circumference of valve stent 222. However, more or fewer suture guides 225 may be used and they need not be equally spaced.

In an embodiment, lock portions 264 of first locking mechanisms 260 are disposed about the interior circumference of valve stent 222 at inflow end 226, as shown in FIG. 10A. More particularly, lock portions 264 of first locking mechanisms 260 are configured to couple to corresponding lock loops 274 of first locking mechanisms 260 in order to couple valve stent 122 to inflow stent 210, as described in greater detail below. In an embodiment, there are three (3) lock portions 264 spaced equally circumferentially about valve stent 122. However, more or fewer lock portions 264 may be used and they need not be equally spaced.

In an embodiment, lock loops 294 of second locking mechanisms 262 are disposed about the interior circumference of valve stent 222 at outflow end 230, as shown in FIG. 10B and described in greater detail below. More particularly, lock loops 294 of second locking mechanisms 262 are configured to couple to corresponding lock portions 284 of second locking mechanisms 262 in order to couple valve stent 222 to outflow stent 240, as described in greater detail below. In an embodiment, there are three (3) lock loops 294 spaced equally circumferentially about the interior of valve stent 222. However, more or fewer lock loops 294 may be used and they need not be equally spaced.

Inflow end 226 of valve stent 222 of valve component 220 is configured to connect to corresponding outflow end 214 of inflow stent 210, and outflow end 230 of valve stent 222 of valve component 220 is configured to connect to a corresponding inflow end 242 of outflow stent 240 when in the radially expanded deployed configuration, as shown in FIG. 7.

Prosthetic valve 234 is disposed within valve lumen 224 of valve stent 222, as shown in FIGS. 7-8 and 10A-10B, and can assume a variety of configurations described in greater detail in, for example, U.S. Pat. No. 8,226,710 to Nguyen, previously incorporated by reference herein. In an embodiment, as shown in FIGS. 10A-10B, prosthetic valve 234 comprises three (3) leaflets 234*a*, 234*b*, 234*c*. However, more or fewer leaflets, such as a bi-leaflet design, may be utilized.

Valve stent 222 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure. Prosthetic valve 234 may be formed of materials as are known in the art and suitable for the purposes of the present disclosure.

Outflow stent 240 is of a generally tubular configuration, and includes a radially compressed delivery configuration and a radially expanded deployed configuration. Outflow stent 240 includes an inflow end 242 and an outflow end 246, and defines an outflow lumen 248 therein. Outflow stent further includes a plurality of suture guides 249, and a plurality of lock portions 284 of second locking mechanisms 262, as shown in FIGS. 7-8 and FIGS. 11A-11B.

Figure 11A:
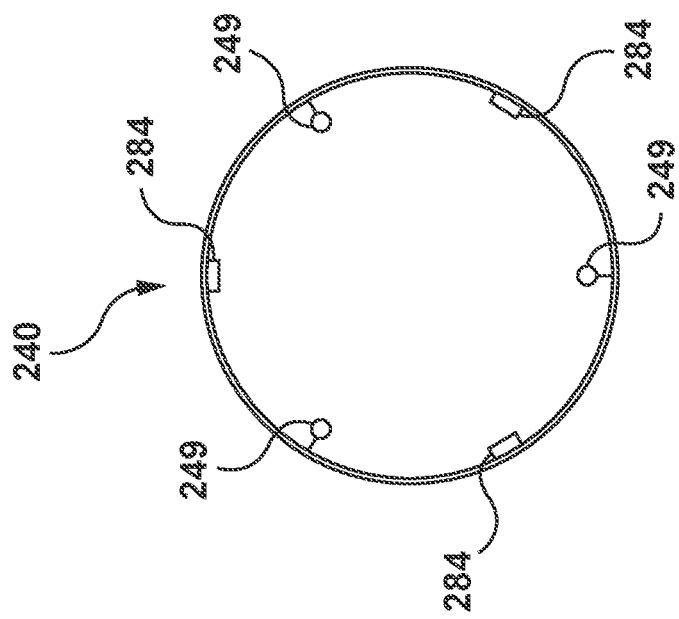
FIG. 11A is an end illustration of the inflow end of the outflow stent of FIG. 7.
Figure 11B:
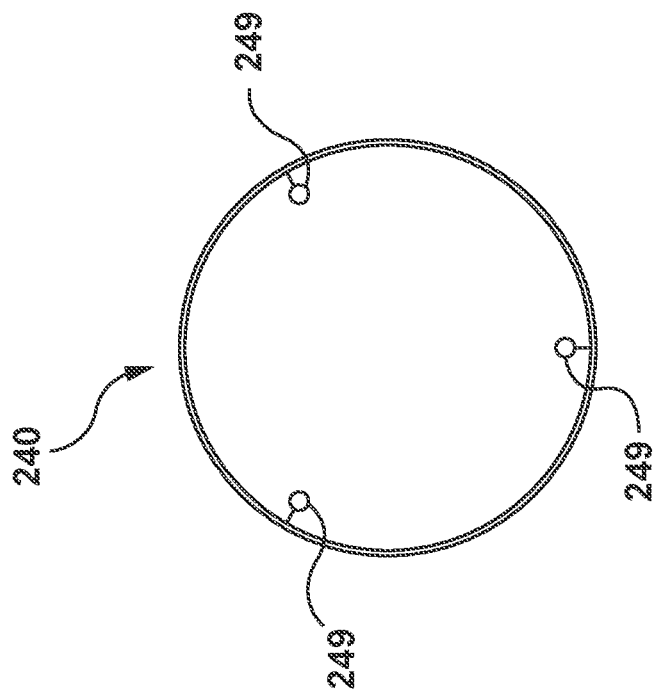
FIG. 11B is an end illustration of the outflow end of the outflow stent of FIG. 7.

In an embodiment, suture guides 249 are disposed about an interior circumference of outflow stent 240, as shown in FIGS. 11A-11B. In an embodiment, a set of suture guides 249 is disposed at inflow end 242 of outflow stent 240, as shown in FIG. 11A, and a set of suture guides 249 is disposed at outflow end 246 of outflow stent 240, as shown in FIG. 11B. Suture guides 249 are configured to retain sutures 250, described below, therethrough. More particularly, suture guides 249 provide routing of sutures 250 through outflow stent 240 and alignment of outflow stent 240 relative to valve component 220 and inflow stent 210. Suture guides 249 may be configured, for example, and not by way of limitation, as rings, hooks, loops, or any other configuration suitable for purposes of the present disclosure. In an embodiment, there are three (3) suture guides 249 equally spaced about the interior circumference of outflow stent 240 at each of the inflow end 242 and the outflow end 246. However, more or fewer suture guides 249 may be used and they need not be equally spaced. Further, they may be disposed other than at the inflow and outflow ends of outflow stent 240.

In an embodiment, lock portions 284 of second locking mechanisms 262 are disposed about the interior circumference of outflow stent 240 at inflow end 242, as shown in FIG. 11A. More particularly, lock portions 284 of second locking mechanisms 262 are configured to couple to corresponding lock loops 294 of second locking mechanisms 262 to couple outflow stent 240 to valve stent 222, as described in greater detail below.

Inflow end 242 of outflow stent 240 is configured to connect to corresponding outflow end 230 of valve stent 222 of valve component 220 when in the radially expanded deployed configuration, as shown in FIG. 7. Outflow stent 240 may be formed, for example, and not by way of limitation, of nickel titanium, Nitinol, nickel-cobalt-chromium-molybdenum (MP35N), stainless steel, high spring temper steel, or any other metal or composite having elastic properties to permit extension and recoil suitable for purposes of the present disclosure.

Figure 12C:
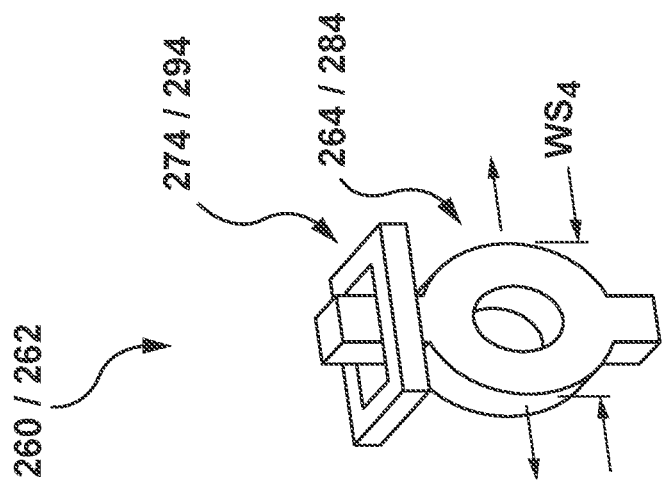
FIG. 12C is a close-up perspective illustration of the locking mechanism of FIG. 12A in a locked configuration.
Figure 12B:
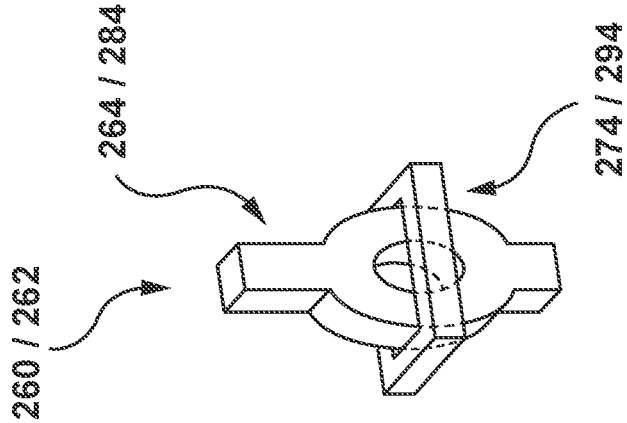
FIG. 12B is a close-up perspective illustration of the locking mechanism of FIG. 12A in a compressed configuration.
Figure 12A:
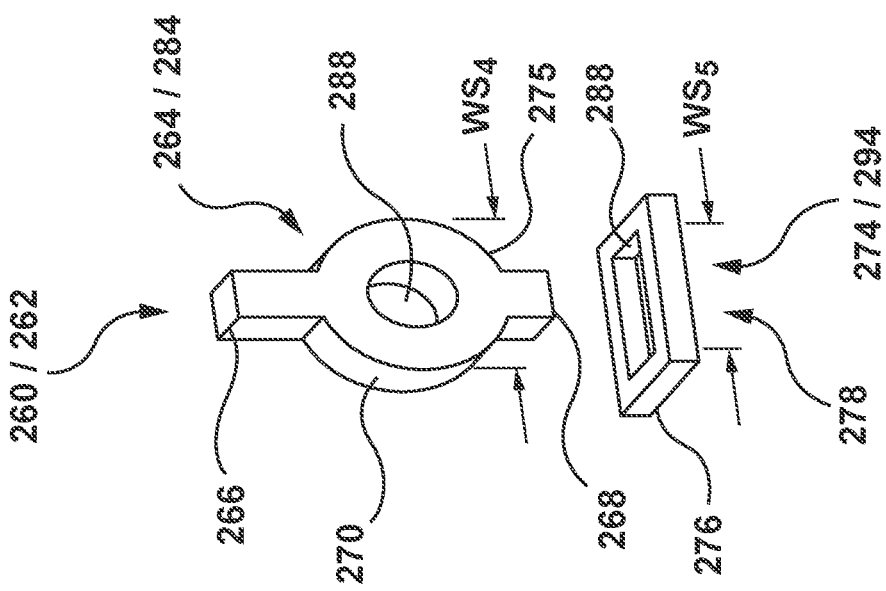
FIG. 12A is a close-up perspective illustration of an embodiment of a locking mechanism of the modular valve prosthesis of FIG. 7 in an unlocked configuration.

As explained above, a set of first locking mechanisms 260 couple inflow stent 210 to valve stent 222, and a set of second locking mechanisms 262 couple valve stent 222 to outflow stent 240. In an embodiment first locking mechanisms 260 and second locking mechanisms 262 are disposed about an interior circumference of respective inflow stent 210, valve stent 222, and outflow stent 240 of modular valve prosthesis 200. First locking mechanisms 260 and second locking mechanisms 262 include an unlocked configuration, a compressed configuration, and a locked configuration. As explained above, and shown in more detail in FIGS. 12A-12C, first and second locking mechanisms 260/262 include lock portions 264/284 and lock loops 274/294, respectively. Lock portions 264/284 include a bulge portion 270 disposed between a proximal end 266 and a distal end 268. Bulge portion 270 may be configured as a ring or loop, as shown in FIGS. 12A-12C. Bulge portion 270 includes an opening 288 extending therethrough such that bulge portion 270 is shaped like a ring or doughnut or torus. Lock portion 264/284 further includes a sloped outer surface 275 between distal end 268 and a widest portion of bulge portion 270 such that distal end 268 has a smaller width than bulge portion 270. Lock loops 274/294 include a frame loop 276 defining a loop lumen 278 therethrough.

Lock portions 264/284 and lock loops 274/294 are configured such that a static width $WS_4$ of bulge portion 270 is greater than a static width $WS_5$ of lumen 278 of lock portions 264/284, as shown in FIG. 12A. Lock portions 264/284 and lock loops 274/294 are further configured such that distal end 268 of lock portions 264/284 fit within loop lumen 278. As lock portion 264/284 is advanced through loop lumen 278, or lock loop 274/294 is advanced over lock portion 264/284, sloped outer surface 275 contacts inner surface 288 of lock loop 274/294 defining loop lumen 278. As lock portion 264/284 continues to advance through loop lumen 278, pressure of inner surface 288 against sloped surface 275 compresses bulge portion 270, reducing the width of opening 288, as shown in FIG. 12B. Lock portions 264/284 and lock loops 274/294 are further configured such that once bulge portion 270 traverses lock loop 274/294, bulge portion 270 expands to its original width $WS_3$ such that lock portion 264/284 and lock loop 274/294 are coupled to one another. Stated another way, lock portion 264/284 may be pressed through lock loop 274/294, and when so pressed therethrough, will couple lock portion 264/284 to lock loop 274/294. Lock portions 264/284 and lock loops 274/294 may be formed, for example, and not by way of limitation, of stainless steel, Nitinol, nylon, polybutester, polypropylene, silk, polyester or other materials suitable for the purposes described herein.

FIGS. 12A-12C show one example of first and second locking mechanisms 260/262. Those skilled in the art would recognize that other locking mechanisms suitable for purposes of the present disclosure may be utilized. For example, and not by way of limitation, the locking mechanisms described with respect to FIGS. 6A-6C above may be utilized.

Figure 8:
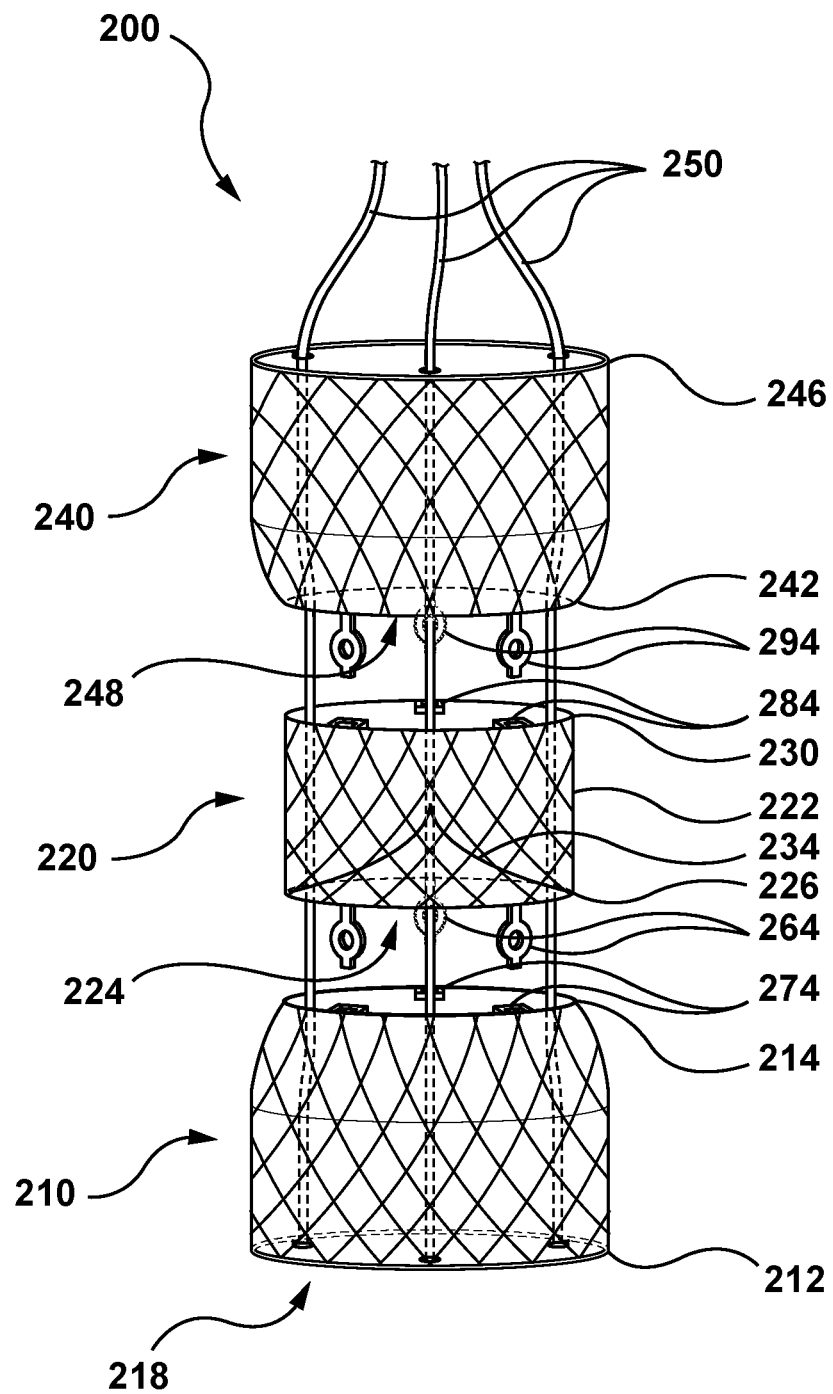
FIG. 8 is a perspective illustration of the modular valve prosthesis of FIG. 7 in a radially expanded deployed configuration, with the modules separated for viewing clarity.

According to embodiments hereof, valve component 220 is configured to be disposed at outflow end 214 of inflow stent 210 and outflow stent 240 is configured to be disposed at outflow end 230 of valve stent 222 of valve component 220, as shown in FIG. 8. More particularly, inflow end 226 of valve stent 222 of valve component 220 is configured to contact outflow end 214 of inflow stent 210, and inflow end 242 of outflow stent 240 is configured to contact outflow end 230 of valve stent 222 of valve component 220 when in the radially expanded deployed configuration. Stated another way, when modular valve prosthesis 200 is in the radially expanded deployed configuration, outflow end 114 is in contact with inflow end 226, and outflow end 230 is in contact with inflow end 242. Outward radial forces of inflow stent 210, valve component 220, and outflow stent 240 imparted against native artery walls when in the modular valve prosthesis 200 is in the radially expanded deployed configuration maintains positioning of modular valve prosthesis 200 within the affected artery and maintains contact of inflow end 226 of valve stent 222 of valve component 220 with outflow end 214 of inflow stent 210, and outflow end 230 of valve stent 222 of valve component 220 with inflow end 242 of outflow stent 240.

FIGS. 7 and 8 also show sutures 250 disposed through the interior of inflow stent 210, valve component 220, and outflow stent 240 of modular valve prosthesis 200. Sutures 250 are shown in FIG. 8 with modular valve prosthesis 200 in the radially expanded deployed configuration with the modules separated for clarity and explanation purposes only. Sutures 250 are coupled to a delivery system, as described below, and are disposed through suture guides 249 of outflow stent 240, suture guides 225 of valve stent 222, and suture guides 219 of inflow stent 210 when modular valve prosthesis 200 is in the radially compressed delivery configuration, such that inflow stent 210, valve component 220, and outflow stent 240 may be properly aligned at a treatment site upon deployment thereof, as shown in FIGS. 7-8 and described in greater detail below. Sutures 250 may be formed, for example, and not by way of limitation, of stainless steel, Nitinol, nylon, polybutester, polypropylene, silk, polyester or other materials suitable for the purposes described herein.

Although two embodiments of a modular valve prosthesis (modular valve prosthesis 100 and modular valve prosthesis 200) have been described above, they are not meant to be limiting. Further, each of the features of modular valve prosthesis 100 can be interchanged with each of the features of modular valve prosthesis 200. For example, and not by way of limitation, the first and second locking mechanisms of each embodiment may be disposed on the exterior of the respective stent or the interior of each respective stent. Further, the first and second locking mechanisms may be aligned with the respective stents (not shown). Further, the locking mechanisms shown in FIGS. 6A-6C may be used with either embodiment or variations thereof, or the locking mechanisms of FIGS. 12A-12C may be used with either embodiment or variations thereof. Further, either embodiment or variations thereof may or may not include flanges.

A delivery system 300 according to an embodiment hereof is shown in FIGS. 13-16B. Delivery system 300 includes a handle 310, an outer sheath 320, an inner shaft 340, a plurality of sutures 350, and a hub assembly 330. Components in accordance with the embodiment of delivery system 300 of FIGS. 13-16B, are described in greater detail below. Various features of the components of delivery system 300 reflected FIGS. 13-16B and described below can be modified or replaced with different structures and or mechanisms. Delivery system 300, described in greater detail below, is merely an exemplary embodiment of a transcatheter delivery system according to embodiment hereof and modifications can be made to the embodiments described herein without departing from the spirit and scope of the present invention. The present disclosure is in no way limited to the handle 310, outer sheath 320, inner shaft 340, sutures 350, and hub assembly 330 shown and described below. Components of delivery system 300 may assume different forms and construction based upon application needs. Further, the systems and functions described below can be implemented in many different embodiments of hardware. Any actual hardware described is not meant to be limiting.

Figure 13:
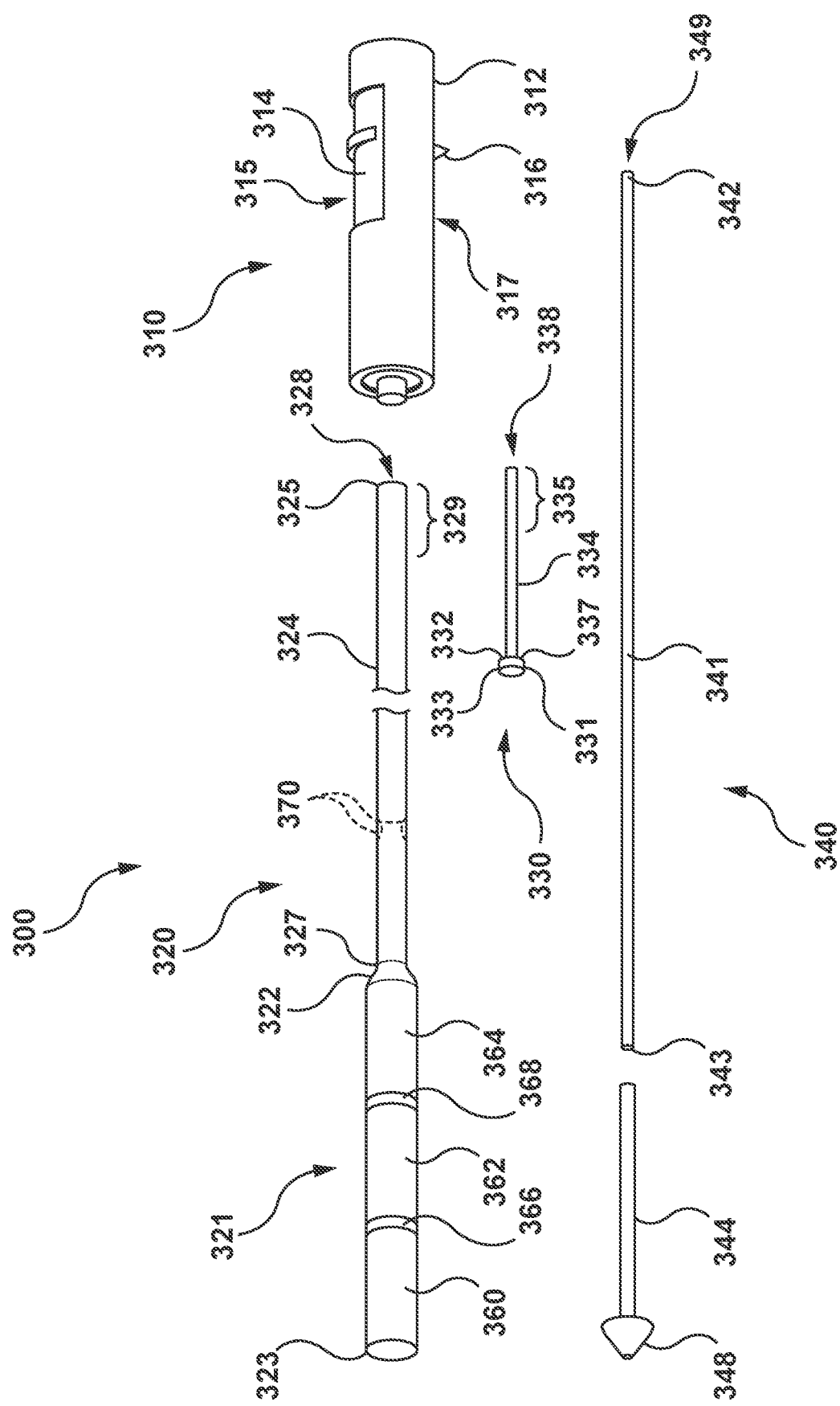
FIG. 13 is exploded perspective illustration of a delivery system according to an embodiment hereof.

Handle 310 includes a housing 312 and a plurality of actuator mechanisms 314/316 retained therein. More particularly, handle 310 is configured to maintain portions of actuator mechanisms 314/316 within a cavity (not shown), defined by housing 312, as shown in FIG. 13. In the embodiment shown in FIG. 13, housing 310 further forms a plurality of longitudinal slots 315/317 (slot 317 is obscured in FIG. 13 by handle housing 312) through which actuator mechanisms 314/316 extend, respectively, for interfacing by a user. Handle 310 provides a surface for convenient handling and grasping by a user, and can have a generally cylindrical shape as shown. While handle 310 of FIG. 13 is shown with a cylindrical shape, it is not meant to limit the design, and other shapes and sizes are contemplated based on the application requirements. Handle 310 can assume a variety of configurations described in greater detail in U.S. Pat. No. 8,579,963 to Tabor, which is incorporated in its entirety by reference herein. Actuator mechanism 314 is generally constructed to provide selective retraction/advancement of outer sheath 320, including a proximal shaft 324 and a capsule 321, and can have a variety of constructions and/or devices capable of providing the desired user interface. Actuator mechanism 316 is generally constructed to provide selective retraction/advancement of hub assembly 330, including a hub shaft 334 and a hub 331, and can have a variety of constructions and/or devices capable of providing the desired user interface.

Figure 14:
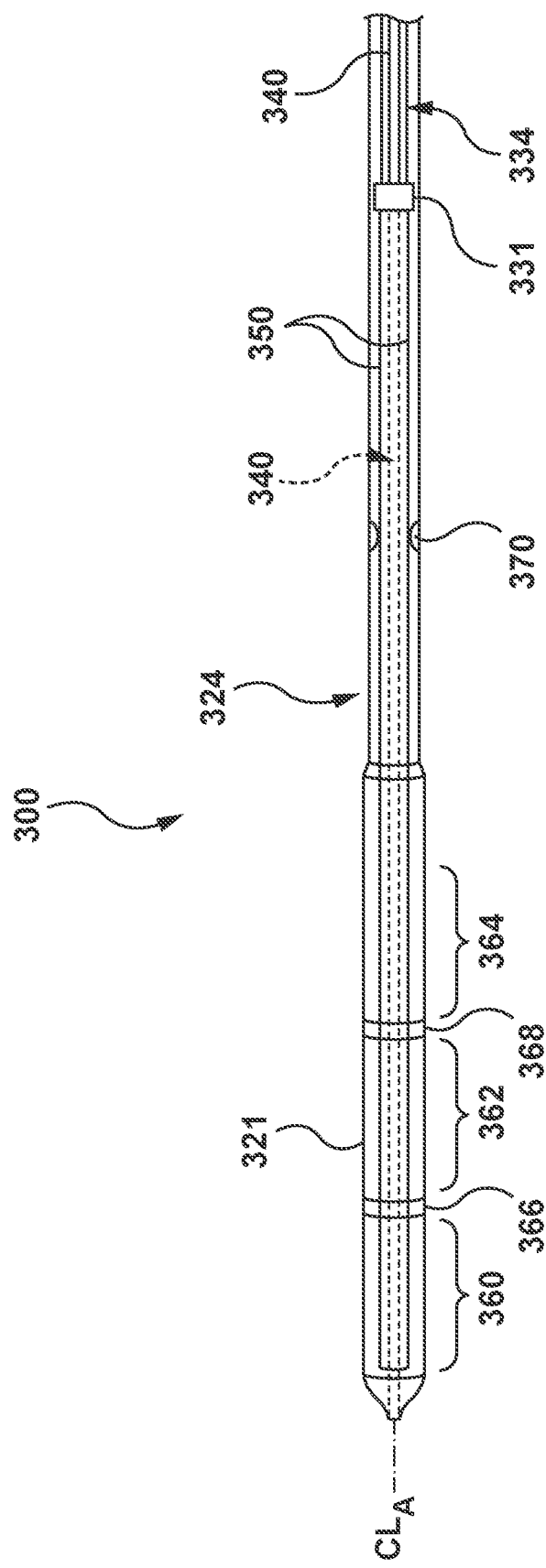
FIG. 14 is a side illustration of a distal portion of the delivery system of FIG. 13.
Figure 15:
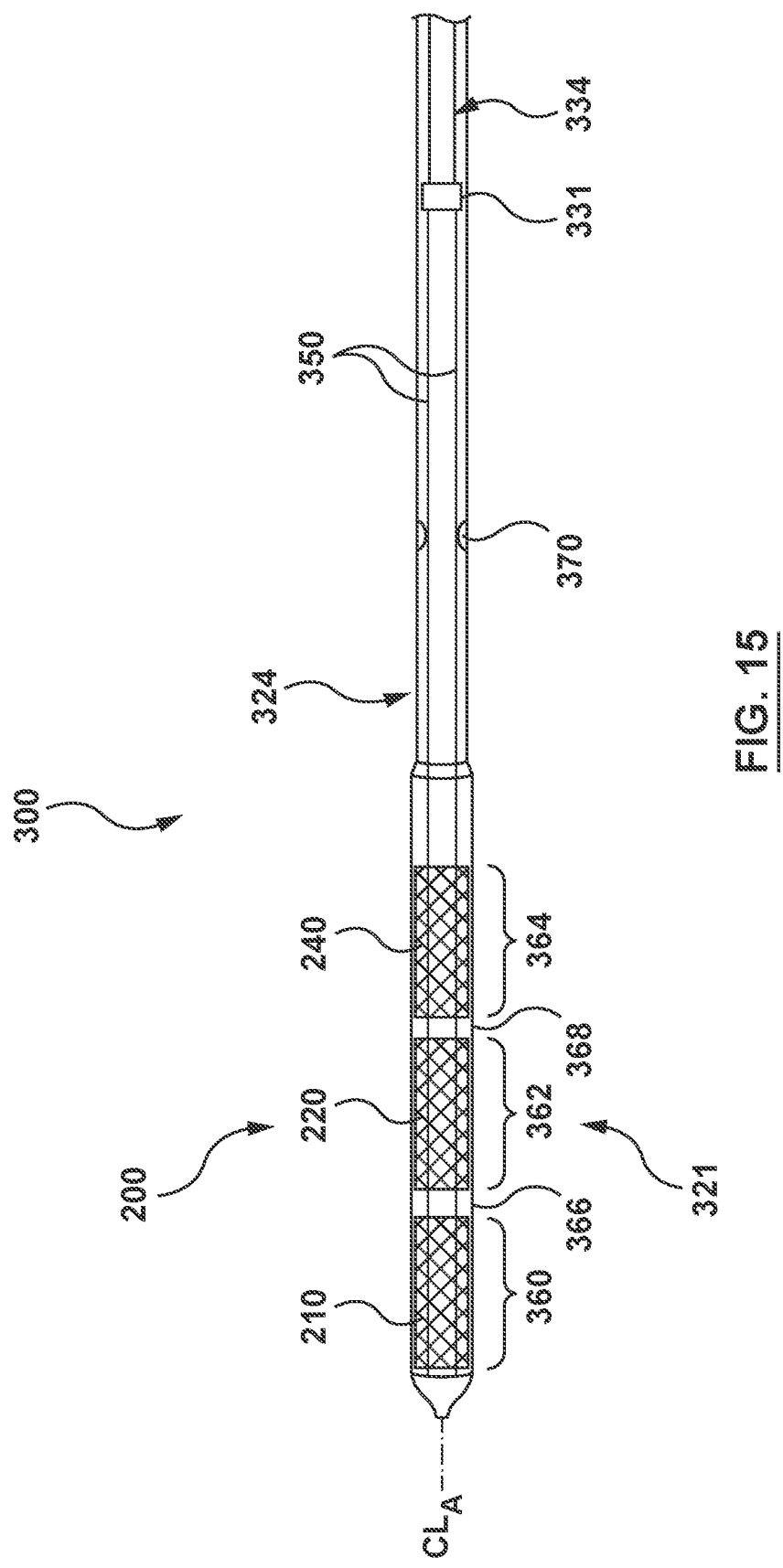
FIG. 15 is side illustration of the distal portion of the delivery system of FIG. 13 with a modular valve prosthesis in a radially collapsed delivery configuration contained within a capsule of the delivery system.

Outer sheath 320 is coaxially and slidably disposed about the outer circumference of hub assembly 330 and inner shaft 340 as shown in FIGS. 14-15. Stated another way, outer sheath 320 may be longitudinally moved relative to hub assembly 330 and inner shaft 340, as described in more detail herein. With reference to FIGS. 13-16B, outer sheath 320 includes capsule 321, a proximal shaft 324, and defines a lumen 328 extending from a proximal end 325 of proximal shaft 324 to a distal end 323 of capsule 321. Outer sheath 320 further includes a suture detaching mechanism 370 described in greater detail below. Although outer sheath 320 is described herein as including capsule 321 and proximal shaft 324, capsule 321 may simply be an extension of proximal shaft 324. The length and thickness of capsule 321 are determined by the requirements of the specific application.

Capsule 321 includes a first section 360, a second section 362, and a third section 364, as shown in FIGS. 14-15. Capsule 321 is configured such that when a modular valve prosthesis, such as modular valve prosthesis 200, is radially compressed within capsule 321 for delivery, inflow stent 210, valve component 220, and outflow stent 240 are aligned with first section 360, second section 362, and third section 364, respectively. Alternatively, inflow stent 210, valve component 220, and outflow stent 240 are aligned with third section 364, second section 362, and first section 360, respectively. Capsule 321 further includes a first band 366 disposed between first section 360 and second section 362, and a second band 368 disposed between second section 362 and third section 364. With modular valve prosthesis 200 radially compressed within capsule 321 for delivery, a first gap 440 disposed between inflow stent 210 and valve component 220 is aligned with first band 366 and a second gap 450 disposed between valve component 220 and outflow stent 240 is aligned with second band 368. Alternatively, depending on the orientation of modular valve prosthesis disposed in capsule 321, first gap 440 disposed between inflow stent 210 and valve component 220 may be aligned with second band 368 and second gap 450 disposed between valve component 220 and outflow stent 240 may be aligned with first band 366. First band 366 is configured to be more flexible that first section 360 and second section 362, and second band 368 is configured to be more flexible that second section 362 and third section 364. For example, and not by way of limitation, first and second bands 366, 368 may be made of a different material than first, second, and third sections 360, 362, 364. For example, and not by way of limitation, first and second bands 366, 368 may be formed from a polymer construction while first, second, and third sections 360, 362, 364 may be metallic. In another non-limiting example, first and second bands 366, 368 may be made from a polymer construction, while first, second, and third sections 360, 362, 364 may be formed from a reinforced polymer construction, such as by adding a metallic braid or weave to the polymer. In another non-limiting example, first and second bands 366, 368 or first, second, and third sections 360, 362, 364 may be treated such that first and second bands 366, 368 are more flexible than first, second, and third sections 360, 362, 364. Although modular valve prosthesis 200 and components thereof are used to describe a modular valve prosthesis disposed within capsule 321, this is not limiting. Other modular valve prostheses, such as modular valve prosthesis 100 or other embodiments not specifically described herein, may also be used. Further, the orientation of the modular valve prosthesis with respect to capsule 321 is not limiting. For example, and not by way of limitation, modular valve prosthesis may be flipped such that inflow stent 210 may be aligned with third section 364 instead of first section 362.

Proximal shaft 324 includes a detaching mechanism 370 coupled therein, as shown in FIGS. 13-16B and described in greater detail below. Proximal shaft 324 is configured for fixed connection to capsule 321 at a connection point 327 at a proximal end 322 of capsule 321 for example, and not by way of limitation, by fusing, welding, adhesive, sutures, or other means suitable for the purposes described herein. Proximal shaft 324 extends proximally from capsule 321 into housing 312 of handle 310, and a proximal portion 329 of proximal shaft 324 is rigidly connected to actuator mechanism 314 of handle 310. Proximal portion 329 is coupled to actuator mechanism 314 such that movement of actuator mechanism 314 causes outer sheath 320 to move relative to inner shaft 340 and hub 331. Proximal shaft 324 may be coupled to actuator mechanism 314, for example, and not by way of limitation by adhesives, welding, clamping, and other coupling devices as appropriate. Outer sheath 320 is thus movable relative to handle 310, inner shaft 340, and hub 331 by actuator mechanism 314. However, if actuator mechanism 314 is not moved and handle 310 is moved, outer sheath 320 moves with handle 310, not relative to handle 310.

Hub assembly 330 is coaxially and slidably disposed between outer sheath 320 and inner shaft 340 as shown in FIGS. 13-16B. Stated another way, hub assembly 330 may be longitudinally moved relative to outer sheath 320 and inner shaft 340 as described in more detail herein. With reference to FIGS. 13-16B, hub assembly 330 includes hub 331 and hub shaft 334, and defines a lumen 338 extending from a proximal end 335 of hub shaft 334 to a distal end 333 of hub 331. Although hub assembly 330 is described herein as including hub 331 and hub shaft 334, hub 331 may simply be an extension of hub shaft 334.

Hub 331 is disposed within lumen 312 of outer sheath 320, between outer sheath 320 and inner shaft 340 as shown in FIGS. 13-15 and shown in greater detail in FIG. 16A-16B. Hub 331 provides a surface for connection of sutures 350 as described in greater detail below. Hub 331 is rigidly connected to hub shaft 334 at a connection point 337 for example, and not by way of limitation, by adhesives, welding, clamping, and other coupling devices as appropriate. Hub 331 can assume a variety of configurations.

Hub shaft 334 is configured for fixed connection to hub 331 at a connection point 337 at a proximal end 332 of hub 331 for example, and not by way of limitation, by fusing, welding, adhesive, sutures, or other means suitable for the purposes described herein. Hub shaft 334 extends proximally from hub 331, with a proximal portion 339 of hub shaft 334 coupled to handle 310, as shown in FIGS. 13-15. More particularly, hub shaft 334 of hub assembly 330 extends proximally into housing 312 of handle 310 and proximal portion 339 of hub shaft 334 is rigidly connected to actuator mechanism 316 of handle 310. Proximal portion 339 is coupled to actuator mechanism 316 such that movement of actuator mechanism 316 causes hub assembly 330 to move relative to inner shaft 340 and outer sheath 320. Hub shaft 334 may be coupled to actuator mechanism 316, for example, and not by way of limitation, by adhesives, welding, clamping, and other coupling devices as appropriate. Hub assembly 330 is thus movable relative to handle 310, inner shaft 340, and outer sheath 320 by actuator mechanism 316. However, if actuator mechanism 316 is not moved and handle 310 is moved, hub assembly 330 moves with handle 310, not relative to handle 310.

Inner shaft 340 extends within lumen 338 of hub assembly 330 and lumen 328 of outer sheath 320, as shown in FIGS. 13-16B. Inner shaft 340 includes a shaft 341, a retention member 344, and a tip 348 as shown in FIG. 15. Shaft 341 extends from a proximal end 342 of shaft 341 to a distal end 343 of shaft 341. Distal end 343 of shaft 341 connects or is attached to retention member 344, and retention member 344 connects or is attached to tip 348. The components of inner shaft 340 combine to define a continuous lumen 349, which is sized to receive an auxiliary component such as a guidewire (not shown). Although inner shaft 340 is described herein as including shaft 341, retention member 344, and tip 348, retention member 344 and tip 348 may simply be extensions of shaft 341. Shaft 341 of inner shaft 340 extends proximally through housing 312 of handle 310, and is rigidly connected to handle 310 such that lumen 349 provides access for auxiliary components (e.g., a guidewire) therein. Shaft 341 may be coupled to handle 310, for example, and not by way of limitation, by adhesives, welding, clamping, and other coupling devices as appropriate. During sliding or longitudinal movement of outer sheath 320 relative thereto, inner shaft 340 is fixed relative to handle 310. Inner shaft 340 can assume a variety of configurations described in greater detail in U.S. Pat. No. 8,579,963 to Tabor, previously incorporated by reference herein.

Sutures 350 are elongated members as previously described and shown in FIGS. 13-15 and in greater detail in FIGS. 16A-16B. Each suture 350 includes a first end 352 and a second end 354. Sutures 350 are disposed within lumen 328 of outer sheath 320. Each suture 350 extends from first end 352 attached to hub 331, distally through outflow stent 240, valve component 220, and inflow stent 210, and loops back proximally through modular valve prosthesis 200 to second end 354, which is also attached to hub 331. Sutures 350 may be formed, for example, and not by way of limitation, of stainless steel, Nitinol, nylon, polybutester, polypropylene, silk, polyester or other materials suitable for the purposes described herein. First and second ends 352/354 of sutures 350 are attached to hub 331 for example, and not by way of limitation, by fusing, welding, adhesives, tying or other methods suitable for the purposes described herein.

A detaching mechanism 370 is disposed about an interior circumference of proximal shaft 324 of outer sheath 320, between capsule 321 and hub 331. Detaching mechanism 370 is configured such that upon retraction of proximal shaft 324, detaching mechanism 370 cuts or detaches a portion 356 of sutures 350 as shown in FIG. 16B. Detaching mechanism 370 may be configured as a circumferential bump extending from an inner surface of proximal shaft 324 towards a central longitudinal axis $CL_a$, and extending around the entire inner circumference of proximal shaft 324, as shown in FIGS. 16A-16B. In other embodiments, detaching mechanism 370 need not be continuous around the entire inner circumference of proximal shaft 324. Instead, detaching mechanism 370 may be a plurality of bumps or protrusions extending from the inner surface of proximal shaft 324 towards the central longitudinal axis $CL_a$. In an embodiment shown in FIGS. 16A-16B, detaching mechanism 370 is configured such that upon retraction of proximal shaft 324, detaching mechanism 370 is retracted proximally towards and contacts hub 331, and thereby severing or detaching a portion 356 of sutures 350, as shown in FIG. 16B. In an embodiment, at least one of first and second ends 352, 354 of each suture 350 remains attached to hub 331 such that sutures 350 are retracted with delivery system 300. Detaching mechanism 370 may be formed as part of proximal shaft 324, or may be attached to proximal shaft 324 for example, and not by way of limitation, by fusing, welding, adhesives, or other methods suitable for the purposes described herein. Further, detaching mechanism 370 is not limited to bumps or protrusions. Instead, other ways to sever or disconnect sutures 350 may be utilized.

While the delivery system of FIGS. 13-16B shows capsule 321 with three sections 360/362/364 and two bands 366, 368, this is not meant to limit the design and more or fewer sections and bands are envisioned based on the application.

While the delivery system of FIGS. 13-16B shows two sutures 350, it is understood that these are cross-sectional or side views such that this embodiment may include more sutures 350, such as three sutures 350 to match the suture guides described above with respect to modular valve prostheses 100, 200. However, it is further understood that more or fewer sutures 350 may be used.

A method of delivering and deploying a modular valve prosthesis utilizing a delivery system, in accordance with an embodiment hereof, is schematically represented in FIGS. 17-21. FIGS. 17-21 show, and the description herein describes, modular valve prosthesis 100 being delivered and deployed using delivery system 300. However, this is not meant to be limiting. In particular, a similar method may be used to deliver and deploy modular valve prosthesis 200 using delivery system 300 or other delivery systems. Further, other delivery systems may be used to delivery and deploy modular valve prosthesis 100 or 200, or other modular valve prostheses.

Figure 17:
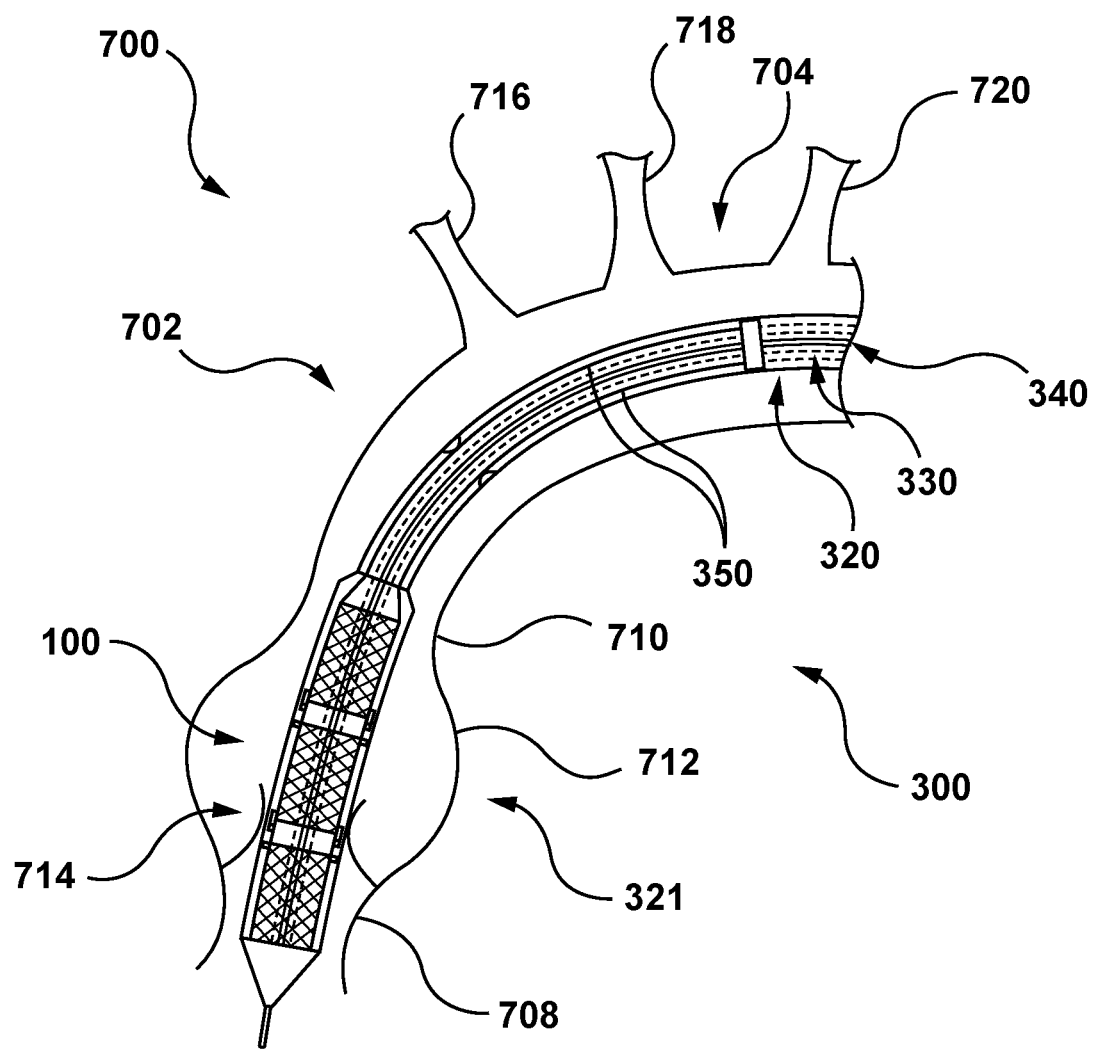
FIGS. 17-21 are simplified illustrations of a method of delivering and deploying a modular valve prosthesis according to an embodiment hereof.

With reference to FIG. 17, using established percutaneous transcatheter delivery procedures, delivery system 300 is introduced into a patient's vasculature and advanced to a treatment site of a damaged or diseased native valve, which in this embodiment is a native aortic valve 714. Delivery system 300 includes a handle (not shown), outer sheath 320, inner shaft 340, hub assembly 330, and sutures 350 as previously described. Capsule 321 of delivery system 300 retains modular valve prosthesis 100 in the radially collapsed delivery configuration, therein. Delivery system 300 is advanced through the aorta 700 (including the aortic arch 704 (passing the innominate or brachiocephalic artery 716, the left common carotid artery 718, and the left subclavian artery 720), ascending aorta 702, sinotubular junction 710, aortic sinuses 712) and to a valve annulus 708 and the site of the damaged or disease native aortic valve 714, as shown in FIG. 17.

Figure 18:
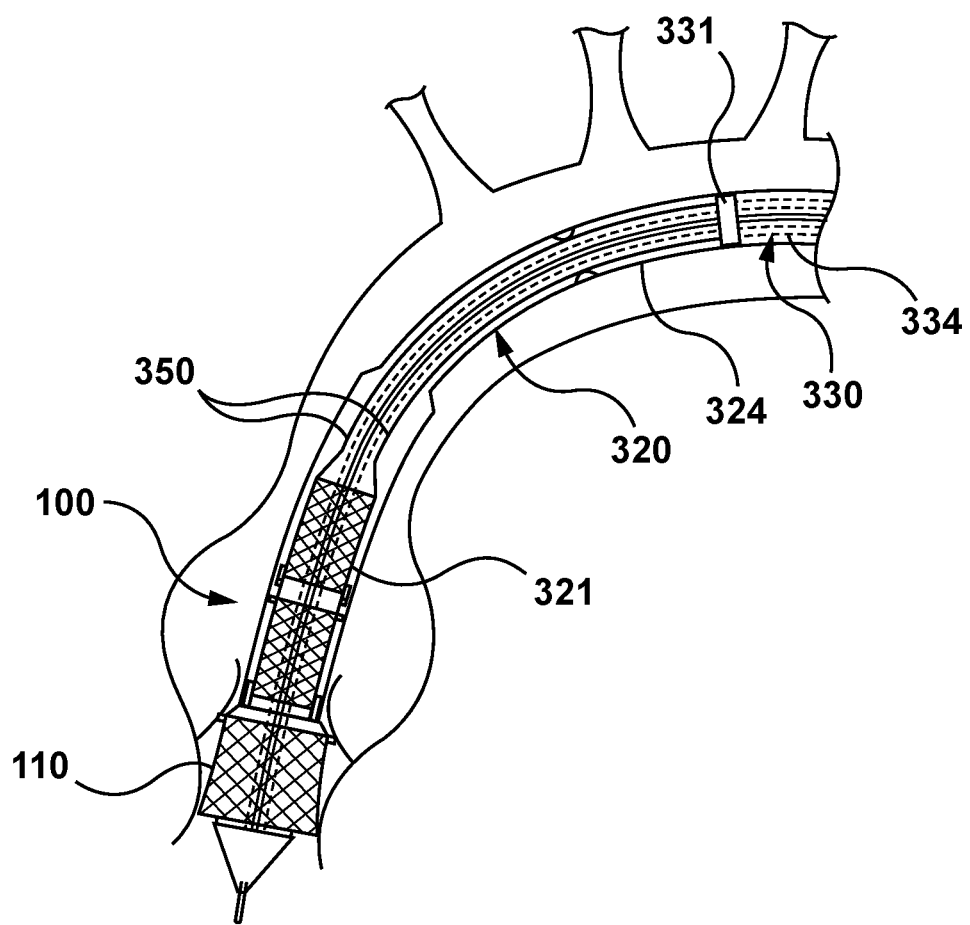

In another step of the method, actuator mechanism 314 of handle 310 (not shown on FIGS. 17-21) is operated proximally to retract outer sheath 320, as shown in FIG. 18. In particular, proximal shaft 324 and capsule 321 are moved proximally to withdraw capsule 321 from its position surrounding inflow stent 110 of modular valve prosthesis 100. As capsule 321 is retracted proximally, inflow stent 110 transitions from the radially compressed delivery configuration to the radially expanded deployed configuration. Capsule 321 is withdrawn sufficiently proximally such that distal edge 323 of capsule 321 is aligned with inflow end 124 of valve component 120.

In another step of the method, actuator mechanism 316 of handle 310 (not shown on FIGS. 17-21) is operated proximally to retract hub assembly 330. In particular, hub shaft 334 and hub 331 are moved proximally to draw sutures 350 taut.

Figure 19:
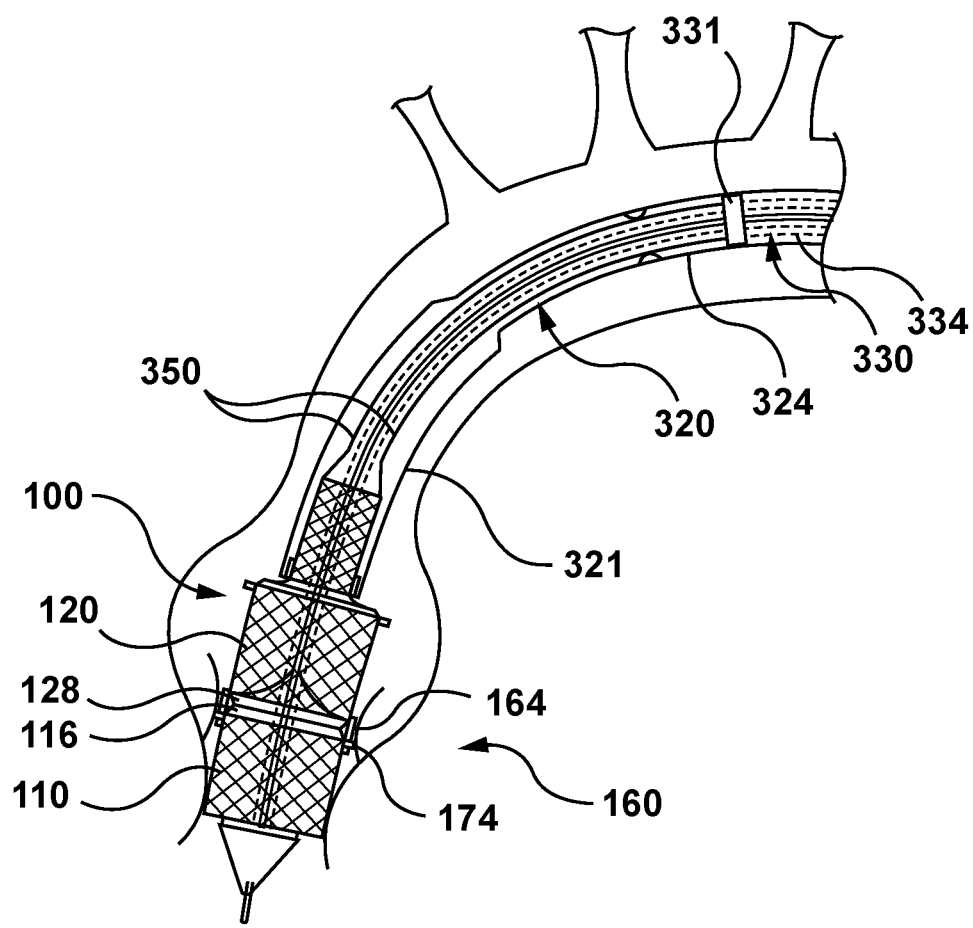

In another step of the method, delivery system 300 is advanced distally to ensure that distal edge 323 of capsule 321 is adjacent outflow end 114 of inflow stent 110. As delivery system 300 is advanced, sutures 350 are maintained taut. In another step of the method, actuator mechanism 314 of handle 310 (not shown on FIGS. 17-21) is operated proximally to further retract outer sheath 320, as shown in FIG. 19. In particular, proximal shaft 324 and capsule 321 are moved proximally to withdraw capsule 321 from its position surrounding valve component 120 of modular valve prosthesis 100. As capsule 321 is retracted proximally, valve component 120 transitions from the radially compressed delivery configuration to the radially expanded deployed configuration, taut sutures 350 align valve component 120 with inflow stent 110, inflow flange 128 of valve component 120 contacts outflow flange 116 of inflow stent 110, and lock portions 164 of first locking mechanisms 160 of valve component 120 couple to lock loops 174 of first locking mechanisms 160 of inflow stent 110. Stated another way, as valve component 120 radially expands, it is aligned with, contacts, and is coupled to inflow stent 110.

In another step of the method, actuator mechanism 346 of handle 310 (not shown on FIGS. 17-21) is operated proximally to retract hub assembly 330. In particular, hub shaft 334 and hub 331 are moved proximally to draw sutures 350 taut.

Figure 20:
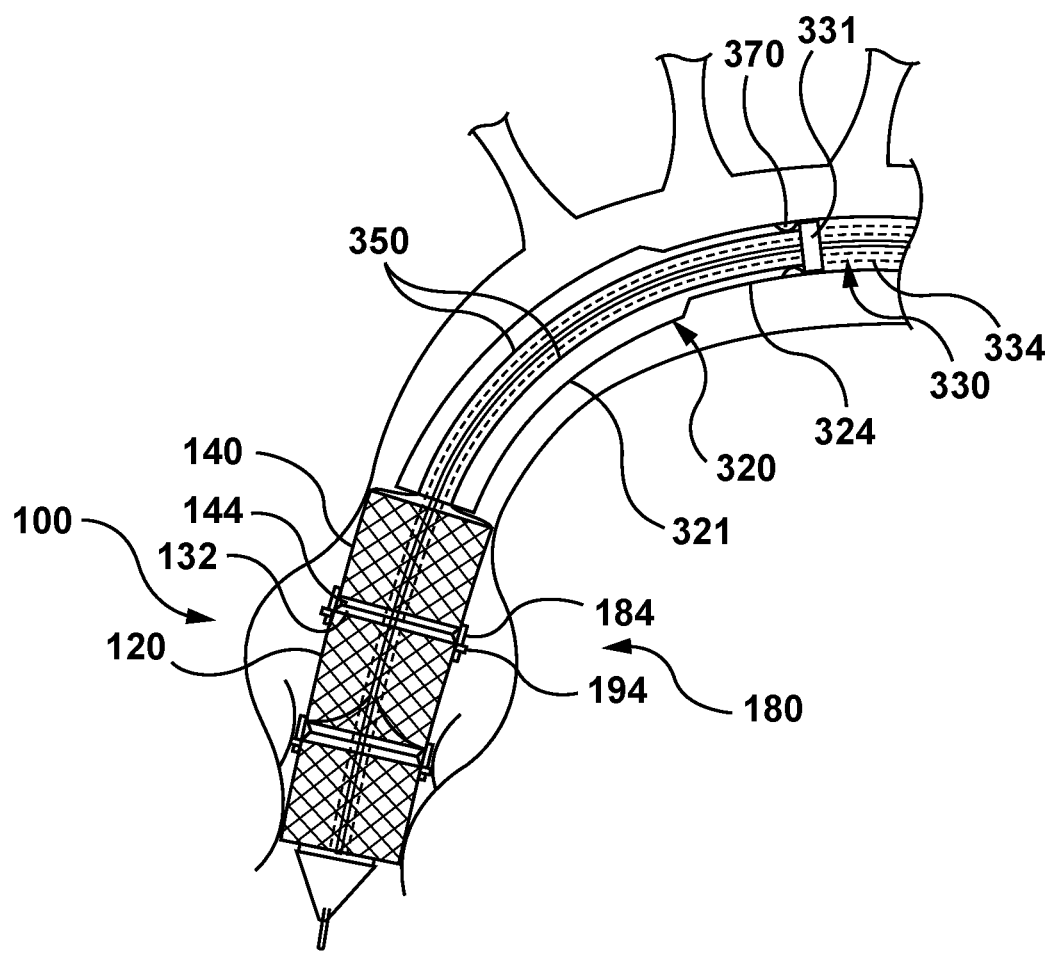

In another step of the method, delivery system 300 is advanced distally to ensure that distal edge 323 of capsule 321 is adjacent outflow end 130 of valve stent 122. As delivery system 300 is advanced, sutures 350 are maintained taut. In another step of the method, actuator mechanism 314 of handle 310 (not shown on FIGS. 17-21) is operated proximally to further retract outer sheath 320, as shown in FIG. 20. In particular, proximal shaft 324 and capsule 321 are moved proximally to withdraw capsule 321 from its position surrounding outflow stent 140 of modular valve prosthesis 100. As capsule 321 is retracted proximally, outflow stent 140 transitions from the radially compressed delivery configuration to the radially expanded deployed configuration, taut sutures 350 align outflow stent 140 with valve component 120, inflow flange 144 of outflow stent 140 contacts outflow flange 132 of valve component 120, and lock portions 184 of second lock mechanisms 162 of outflow stent 140 couple to lock loops 194 of second lock mechanisms 162 of valve component 120. Stated another way, as outflow stent 140 radially expands, it is aligned with, contacts, and is coupled to valve component 120.

In another step of the method, actuator mechanism 314 of handle 310 (not shown on FIGS. 17-21) is operated proximally to further retract outer sheath 320. In particular, proximal shaft 334 and detaching mechanism 370 are moved proximally until detaching mechanisms 370 detach/sever portion 356 of sutures 350.

Figure 21:
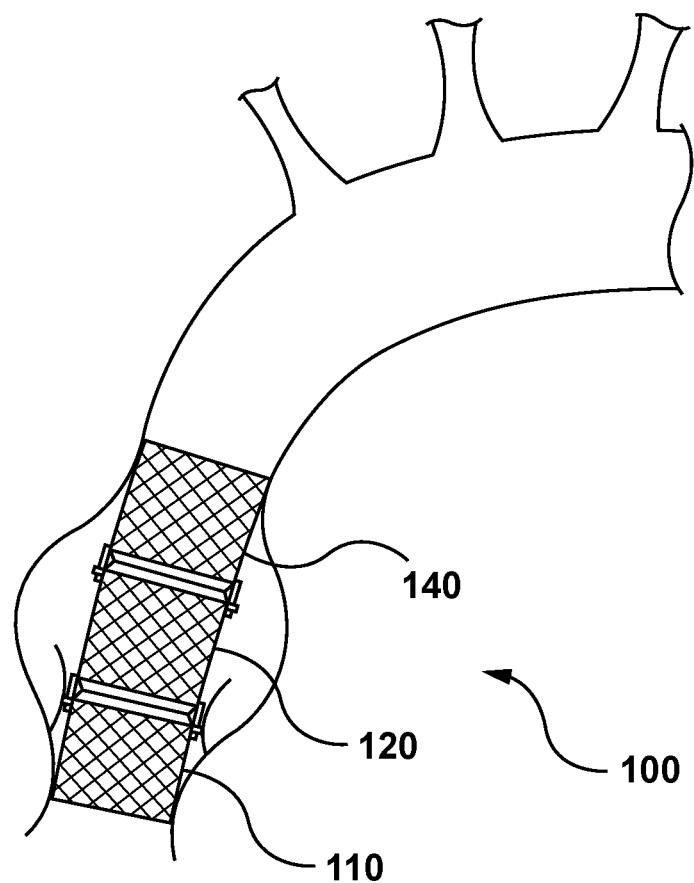

In another step of the method, delivery system 300, with sutures 350 attached thereto, is removed from the patient's vasculature using established percutaneous transcatheter procedures. Modular valve prosthesis 100, including inflow stent 110, valve component 120, and outflow stent 14, remains positioned at the treatment site, as shown in FIG. 21.

While the method of FIGS. 17-21 describe a method for deploying a modular valve prosthesis 100 with three modules, this is not meant to limit the design and a similar method may be employed for modular valve prostheses with more or fewer modules by adding or deleting the steps of actuating actuator mechanism 316 of handle 310 proximally to retract hub assembly 330 and actuating actuator mechanism 314 of handle 310 proximally to further retract outer sheath 320 and release the next module.

While the method of FIGS. 17-21 describes a method for deploying modular valve prosthesis 100 including first locking mechanisms 160 and second locking mechanisms 162, this is not meant to limit the design and other configurations are anticipated including modular valve prostheses with no first or second locking mechanisms. Further, modular valve prostheses without flanges 116, 118, 128, and 132 may be used, such as, but not limited to, modular valve prosthesis 200.

Further, while the method of FIGS. 17-21 describes a method for deploying a modular valve prosthesis by accessing a native aortic valve site via the aorta, the method may be used to treat other valves, such as but not limited to, the mitral valve. Further, other access routes may be used, such as but not limited to, trans-apical, trans-atrial, trans-septal, and other access routes known to those skilled in the art.

While only some embodiments have been described herein, it should be understood that it has been presented by way of illustration and example only, and not limitation. Various changes in form and detail can be made therein without departing from the spirit and scope of the invention, and each feature of the embodiments discussed herein, and of each reference cited herein, can be used in combination with the features of any other embodiment. All patents and publications discussed herein are incorporated by reference herein in their entirety.

What is claimed is:

1. A modular valve prosthesis comprising:
an inflow stent having an inflow end and an outflow end;
a valve component including a valve stent and a prosthetic valve coupled to the valve stent such that the prosthetic valve is disposed in an interior lumen of the valve stent, the valve stent having an inflow end and an outflow end, wherein the inflow end of the valve stent faces the outflow end of the inflow stent;
an outflow stent having an inflow end and an outflow end, wherein the inflow end of the outflow stent faces the outflow end of the valve stent; and
a plurality of elongated members extending longitudinally through the inflow stent, the valve stent, and the outflow stent in a delivery configuration,
wherein in the delivery configuration, the inflow end of the valve stent is not in contact with the outflow end of the inflow stent and the outflow end of the valve stent is not in contact with the inflow end of the outflow stent,
wherein in a radially expanded deployed configuration, the inflow end of the valve stent is in contact with the outflow end of the inflow stent and the outflow end of the valve stent is in contact with the inflow end of the outflow stent, and
wherein the plurality of elongated members are configured to be maintained taut during deployment of the modular valve prosthesis as the valve stent is brought into contact with the inflow stent and the outflow stent is brought into contact with the valve stent.

2. The modular valve prosthesis of claim 1, wherein the plurality of elongated members are sutures.

3. The modular valve prosthesis of claim 1, wherein the inflow end of the valve stent includes a flange that contacts a corresponding flange of the inflow stent in the radially expanded deployed configuration.

4. The modular valve prosthesis of claim 3, wherein the outflow end of the valve stent includes a flange that contacts a corresponding flange of the outflow stent in the radially expanded deployed configuration.

5. The modular valve prosthesis of claim 4, wherein the flanges comprise a first material selected from the group consisting of silicone, fabric, polyester, rubber based materials, tissue/pericardium, and a foam/open cell structure, and wherein the valve stent, the inflow stent, and the outflow stent comprise a second material different than the first material.

6. The modular valve prosthesis of claim 1, further comprising a locking mechanism disposed between the inflow stent and the valve stent such that when the outflow end of the inflow stent is in contact with the inflow end of the valve stent in the radially expanded deployed configuration, the locking mechanism locks the inflow stent and the valve stent together.

7. A modular valve prosthesis comprising:
an inflow stent having an inflow end and an outflow end;
a valve component including a valve stent and a prosthetic valve coupled to the valve stent such that the prosthetic valve is disposed in an interior lumen of the valve stent, the valve stent having an inflow end and an outflow end, wherein the inflow end of the valve stent faces the outflow end of the inflow stent;
an outflow stent having an inflow end and an outflow end, wherein the inflow end of the outflow stent faces the outflow end of the valve stent;
a first locking mechanism coupling the inflow stent to the valve stent, wherein the first locking mechanism includes a first lock loop extending radially with respect to a central longitudinal axis of the modular valve prosthesis and a first lock portion; and
a second locking mechanism coupling the inflow stent to the valve stent, wherein the second locking mechanism includes a second lock loop extending radially with respect to the central longitudinal axis of the modular valve prosthesis and a second lock portion,
wherein in a radially compressed delivery configuration, the first lock portion is longitudinally separated from the first lock loop and the second lock portion is longitudinally separated from the second lock loop, and
wherein in a radially expanded deployed configuration, the first lock portion is disposed through the first lock loop and interlocked therewith, and the second lock portion is disposed through the second lock loop and interlocked therewith.

8. The modular valve prosthesis of claim 7, wherein the first lock portion comprises a first leg and a second leg extending generally longitudinally and parallel to each other, the first leg comprising a first shoulder and the second leg comprising a second shoulder, wherein the first leg and the second leg are configured to compress towards each other to pass through the first lock loop and then separate such that the first shoulder and the second shoulder interlock the first lock portion with the first lock loop.

9. The modular valve prosthesis of claim 8, wherein the second lock portion comprises a third leg and a fourth leg extending generally parallel to each other, the third leg comprising a third shoulder and the fourth leg comprising a fourth shoulder, wherein the third leg and the fourth leg are configured to compress towards each other to pass through the second lock loop and then separate such that the third shoulder and the fourth shoulder interlock the second lock portion with the second lock loop.

10. The modular valve prosthesis of claim 7, wherein the first lock loop and the second lock loop each extend radially inward towards the central longitudinal axis.

11. The modular valve prosthesis of claim 7, wherein the first lock loop and the second lock loop each extend radially outward away from the central longitudinal axis.

12. The modular valve prosthesis of claim 7, wherein the first lock portion comprises a first ring having a first bulge portion, wherein the first bulge portion is configured to compress to pass through the first lock loop and then expand such that the first bulge portion interlocks the first lock portion with the first lock loop.

13. The modular valve prosthesis of claim 12, wherein the second lock portion comprises a second ring having a second bulge portion, wherein the second bulge portion is configured to compress to pass through the second lock loop and then expand such that the second bulge portion interlocks the second lock portion with the second lock loop.

* * * * *